US011707198B2

(12) United States Patent
Eggers et al.

(10) Patent No.: US 11,707,198 B2
(45) Date of Patent: Jul. 25, 2023

(54) WEARABLE APPARATUS, SYSTEM AND METHOD FOR DETECTION OF CARDIAC ARREST AND ALERTING EMERGENCY RESPONSE

(71) Applicant: Eggers & Associates, Inc., Dublin, OH (US)

(72) Inventors: Philip E. Eggers, Dublin, OH (US); Eric A. Eggers, Portland, OR (US); Benjamin Z. Bailey, Athens, OH (US); Andrew Eggers, Shade, OH (US)

(73) Assignee: Eggers & Associates, LLC, Dublin, OH (US)

( * ) Notice: Subject to any disclaimer, the term of this patent is extended or adjusted under 35 U.S.C. 154(b) by 0 days.

(21) Appl. No.: 17/449,333

(22) Filed: Sep. 29, 2021

(65) Prior Publication Data
US 2022/0022758 A1    Jan. 27, 2022

Related U.S. Application Data

(63) Continuation of application No. 15/157,435, filed on May 18, 2016, now Pat. No. 11,219,373, and a
(Continued)

(51) Int. Cl.
| | |
|---|---|
| *A61B 5/0205* | (2006.01) |
| *A61B 5/11* | (2006.01) |
| *A61B 5/024* | (2006.01) |
| *A61B 8/06* | (2006.01) |
| *A61B 5/00* | (2006.01) |

(Continued)

(52) U.S. Cl.
CPC .......... *A61B 5/0205* (2013.01); *A61B 5/0022* (2013.01); *A61B 5/0245* (2013.01); *A61B 5/02416* (2013.01); *A61B 5/02438* (2013.01); *A61B 5/1112* (2013.01); *A61B 5/681* (2013.01); *A61B 5/746* (2013.01); *A61B 5/7455* (2013.01);
(Continued)

(58) Field of Classification Search
None
See application file for complete search history.

(56) References Cited

U.S. PATENT DOCUMENTS

| | | | |
|---|---|---|---|
| 5,830,137 A | * | 11/1998 | Scharf ................. A61B 5/14552 600/323 |
| 2002/0082489 A1 | * | 6/2002 | Casciani ............. A61B 5/14542 600/323 |

(Continued)

*Primary Examiner* — Daniel L Cerioni
*Assistant Examiner* — Benjamin S Melhus
(74) *Attorney, Agent, or Firm* — Emerson, Thomson & Bennett, LLC; Jerry K. Mueller, Jr.

(57) ABSTRACT

The disclosure provides wearable cardiac arrest detection and alerting device that incorporates a non-invasive sensor based on optical and/or electrical signals transmitted into and received from human tissue containing blood vessels, and that transcutaneously quantifies the wearer's heart rate. The heart-rate quantification enables the detection of the absence of any heart beat by the wearable detection and alerting device indicative of the occurrence of a cardiac arrest, wherein the heart is no longer achieving effective blood circulation in the individual wearing the device. The display on the wearable cardiac arrest detection and alerting device may include the elapsed time since the time of detection of a heart rate that is below a predetermine lower limit value, i.e., the detected occurrence of a cardiac arrest event.

18 Claims, 11 Drawing Sheets

Related U.S. Application Data continuation-in-part of application No. 14/970,801, filed on Dec. 16, 2015, now abandoned.

(51) Int. Cl.

| | |
|---|---|
| *G16H 40/63* | (2018.01) |
| *A61B 5/0245* | (2006.01) |
| *G16H 50/30* | (2018.01) |
| *G16H 50/20* | (2018.01) |
| *A61B 8/08* | (2006.01) |
| *G16H 40/67* | (2018.01) |
| *A61B 5/026* | (2006.01) |
| *A61B 7/00* | (2006.01) |
| *A61B 5/0531* | (2021.01) |
| *A61B 5/021* | (2006.01) |
| *A61B 8/00* | (2006.01) |

(52) U.S. Cl.
CPC ............ *A61B 8/06* (2013.01); *A61B 8/488* (2013.01); *G16H 40/63* (2018.01); *G16H 40/67* (2018.01); *G16H 50/20* (2018.01); *G16H 50/30* (2018.01); *A61B 5/021* (2013.01); *A61B 5/02055* (2013.01); *A61B 5/0261* (2013.01); *A61B 5/0531* (2013.01); *A61B 5/7207* (2013.01); *A61B 5/7282* (2013.01); *A61B 7/003* (2013.01); *A61B 8/4227* (2013.01); *A61B 2560/0214* (2013.01); *A61B 2560/0219* (2013.01); *A61B 2562/0219* (2013.01)

(56) References Cited

U.S. PATENT DOCUMENTS

| | | | |
|---|---|---|---|
| 2009/0322513 A1* | 12/2009 | Hwang | H04W 4/90 600/301 |
| 2015/0366518 A1* | 12/2015 | Sampson | A61B 5/7275 600/509 |
| 2016/0093197 A1* | 3/2016 | See | G08B 25/10 340/539.12 |
| 2018/0174680 A1* | 6/2018 | Sampath | G16H 40/00 |

\* cited by examiner

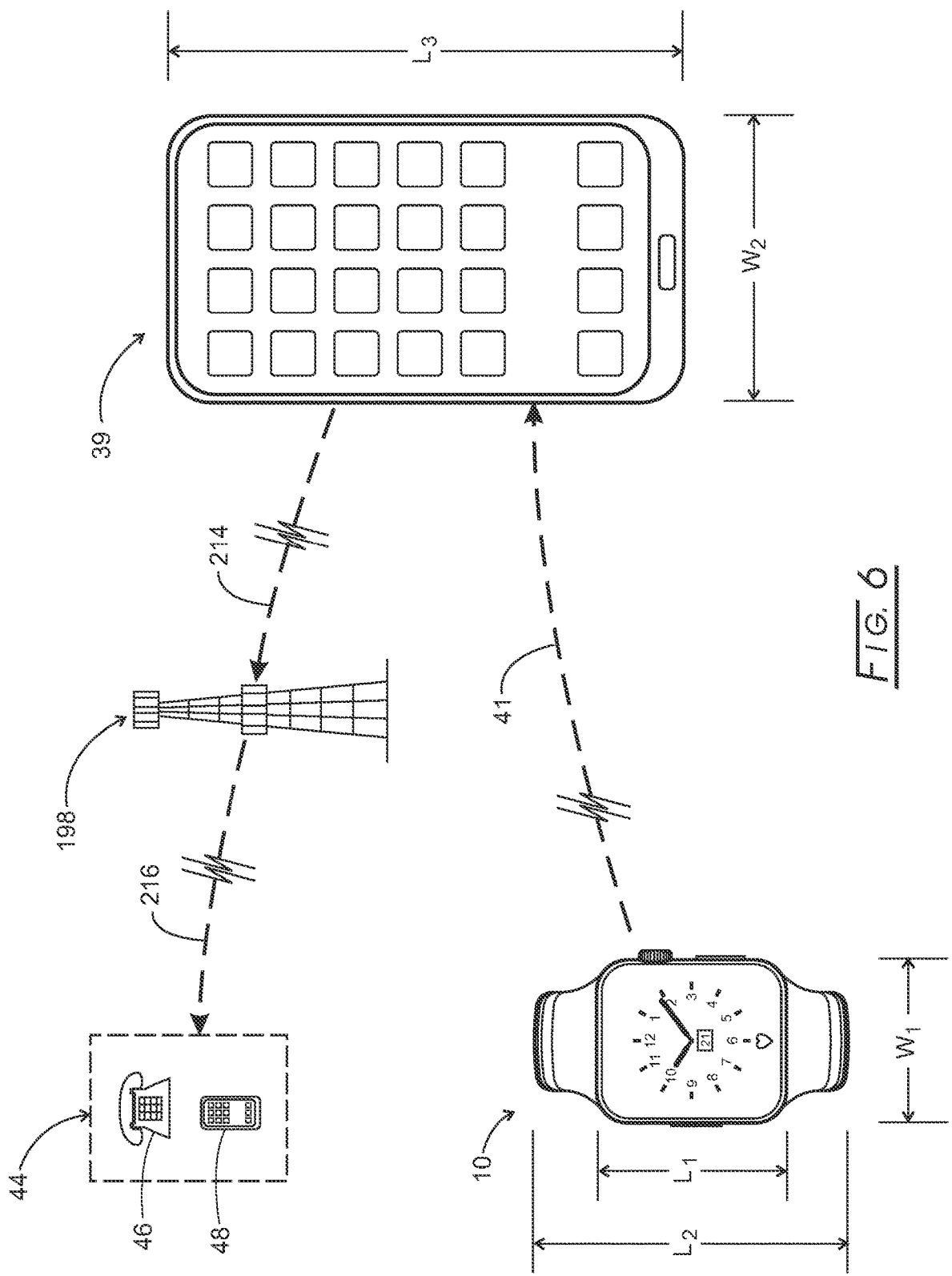

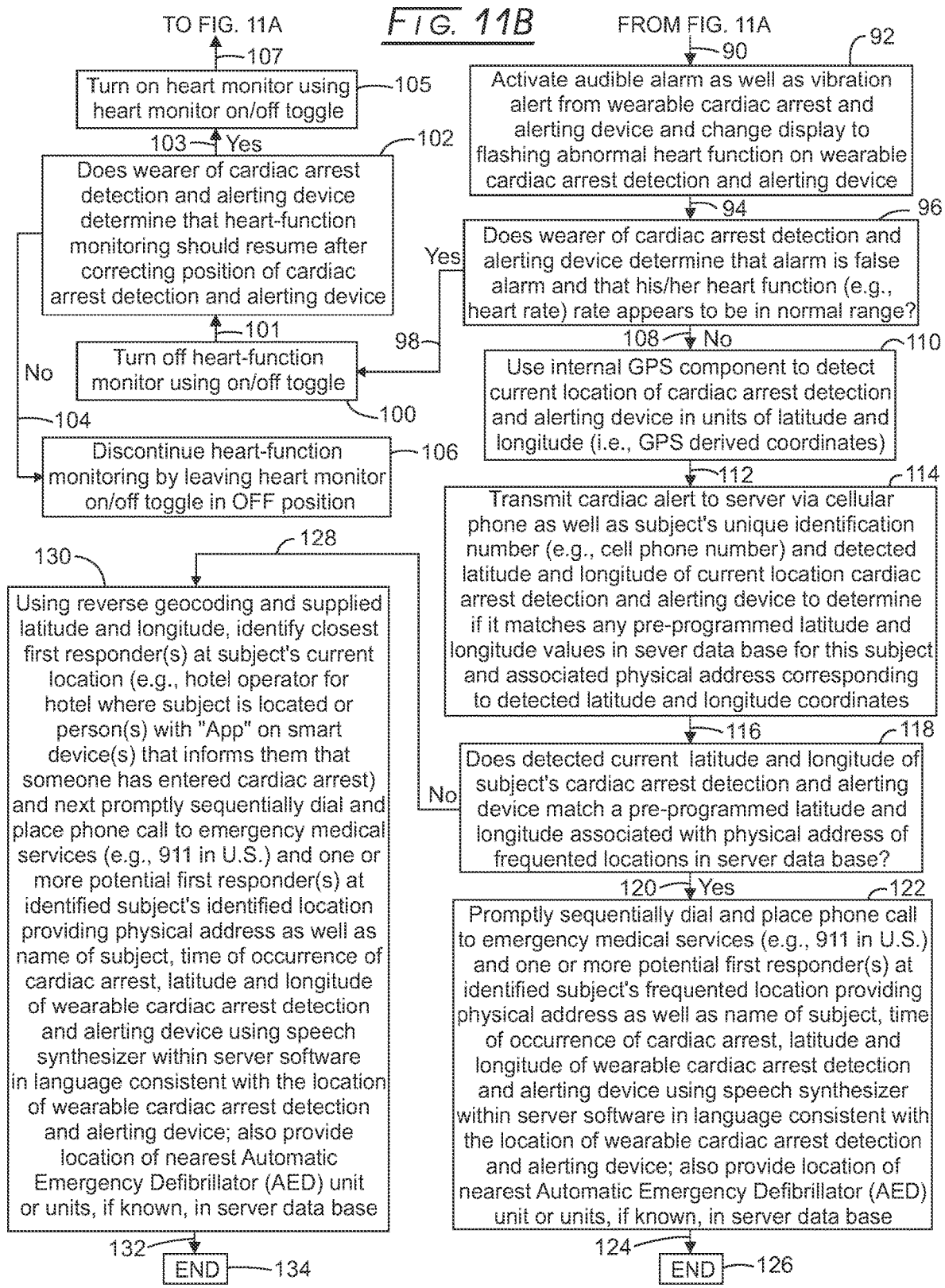

WEARABLE APPARATUS, SYSTEM AND METHOD FOR DETECTION OF CARDIAC ARREST AND ALERTING EMERGENCY RESPONSE

CROSS-REFERENCE TO RELATED APPLICATIONS

This application is a continuation of U.S. patent application Ser. No. 15/157,435, now, U.S. Pat. No. 11,219,373, which is a continuation-in-part of U.S. patent application Ser. No. 14/970,801, filed Dec. 16, 2015, and claimed benefit of provisional application Ser. No. 62/095,239 filed on Dec. 22, 2014.

FIELD

The field of this disclosure is an apparatus, system, and method for the detection of the occurrence of cardiac arrest in a human subject followed by the prompt issuance of an audible alarm, as well as a vibration (i.e., haptic) alert and cellular phone transmission of synthesized speech alerts and location of human subject to pre-determined list or alternative list of phone numbers according to a precise Global Positioning Satellite (GPS) derived location of subject. The verbal alerts would be issued to one or more persons and emergency medical services that are capable of providing life saving interventions (referred to hereinafter as "first responders").

BACKGROUND

Cardiac arrest, also known as cardiopulmonary arrest or circulatory arrest, is a sudden stop in effective blood circulation due to failure of the heart to contract effectively or at all. Medical personnel may refer to an unexpected cardiac arrest as a "sudden cardiac arrest" (SCA).

A cardiac arrest is different from, but may be caused by, a heart attack, where blood flow to the muscle of the heart is impaired. It is different from congestive heart failure wherein the blood circulation level is below normal, but the heart is still pumping sufficient blood to sustain life. It is known that a number of risk factors can contribute to one of the principal causes of cardiac arrest, viz., a delayed repolarization of the heart following a heart beat, an effect known as the Long QT Syndrome. Risk factors for the Long QT Syndrome include, for example, liver or renal impairment, family history of Long QT Syndrome, pre-existing cardiovascular disease, electrolyte imbalance, and interacting drugs such as common antibiotics.

Arrested blood circulation associated with cardiac arrest prevents delivery of oxygen and glucose to the body. The lack of oxygen and glucose to the brain is associated with a loss of consciousness and abnormal or absent breathing. Brain injury is likely to occur if cardiac arrest goes untreated for more than about four to five minutes. It is widely known that the chance of survival decreases about 10% for each minute that arrested blood circulation persists. The best chance of survival and neurological recovery requires prompt and decisive treatment to restore the circulation of blood and glucose to the brain, as well as other organs. Unfortunately, the average elapsed time from the moment that a call is placed to a medical emergency service (e.g., service often associated with closest fire station to individual experiencing a cardiac arrest) to the time of their arrival to treat the individual who has experienced a cardiac arrest is about 8 to 10 minutes. A delay of 8 to 10 minutes until emergency medical personnel arrive and initiation of cardiopulmonary resuscitation (CPR) and/or external defibrillation following cardiac arrest most often results in death or severe morbidity of individual who has experienced a cardiac arrest.

Sudden cardiac death (SCD) accounts for about 15% of all deaths in Western countries with a total of 330,000 deaths per year in the United States. The lifetime risk of sudden cardiac death in the U.S. is about 17% and is three times greater in men than in women. However, beyond the age of 85, this gender difference in sudden cardiac deaths disappears.

The most effective treatment for cardiac arrest is the immediate application of electrical current to the chest region containing the heart, a procedure known as defibrillation. Cardiopulmonary resuscitation (CPR) is used alone or in combination with defibrillation to provide circulatory support and/or to induce an effective heart rhythm. In the past, defibrillator devices have been only used by trained emergency response personnel who arrived at the location of the individual who suffered a cardiac arrest, as well as medical staff if the cardiac arrest has occurred while the individual is in the hospital or skilled nursing care facility.

However, automated versions of a defibrillator, known as an "automated external defibrillator" (AED) are now widely available. An AED is a portable electronic device that automatically diagnoses the life-threatening cardiac arrhythmias of ventricular fibrillation and ventricular tachycardia in a subject and is able to treat them through defibrillation, the application of electrical therapy which restarts the heart function and/or stops the arrhythmia, allowing the heart to re-establish an effective rhythm to enable essential circulation of blood to the brain and other organs. With simple audio and visual commands, newer versions of AEDs are designed to be simple enough for use by a layperson and the use of AEDs is taught in first aid, certified first responder, and basic life support level CPR classes. Also, the newer versions of AEDs manufactured since 2003 utilize biphasic algorithms that produce two sequential lower-energy shocks of 120 to 200 joules, with each shock moving in an opposite current-flow direction between externally applied electrode pads. This lower-energy waveform has been clinically proven to be more effective in re-establishing an effective heart rhythm, as well as offering a reduced rate of complications and reduced recovery time. Some of the latest versions of AEDs have received allowance by the Food and Drug Administration (FDA) for purchase directly by the public in the U.S. without a prescription or without initial purchase by qualified medical personnel. For example, a complete portable AED system manufactured by Phillips (Phillips HeartStart Home Defibrillator) is available online from Amazon at a price of about $1,100 based on pricing in 2015.

Automated external defibrillators now are easy enough to use that most states in the United States include the "good faith" use of an AED by any person under the Good Samaritan laws. "Good faith" protection under a Good Samaritan law means that a volunteer responder (not acting as a part of one's occupation) cannot be held civilly liable for the harm or death of a victim by providing improper or inadequate care, given that the harm or death was not intentional and the responder was acting within the limits of their training and in good faith. In the United States, Good Samaritan laws provide some protection for the use of AEDs by trained and untrained responders. In addition to Good Samaritan laws, Ontario, Canada also has the Chase McEachern Act (Heart Defibrillator Civil Liability) that passed in June, 2007 that protects individuals from liability for damages that may occur from their use of an AED to save someone's life at the immediate scene of an emergency unless damages are caused by gross negligence.

Although widely available CPR training and fully automated AED technology now exists to provide for prompt intervention when an individual suffers a cardiac arrest and becomes unconscious, there remains an unmet need to alert family member(s), neighbor(s), office workers, assisted-living or skilled nursing facility staff, and emergency services at the moment a cardiac arrest has occurred. By way of example, someone may be in his or her office at a place of employment and behind a closed door when a cardiac arrest has occurred. As a result, even though an AED device may be present in the office and co-workers trained in its use, as well as the performance of CPR, no one in the office may become aware during the first critical minutes following the onset of a cardiac arrest, thereby leading to sudden cardiac death. This same situation can occur in many other settings, including, for example, the home, hotel, assisted-living facility, skilled-nursing facility, or other settings where life preserving intervention is immediately available, if potential responders can be alerted to the occurrence of a cardiac arrest in their midst. In addition, many elderly individuals live alone well into their 80's and some even into their 90's, so the need to alert potential responders in their neighborhood, as well as emergency services via a 911 call, is even more critical in the event the occurrence of a cardiac arrest.

The present disclosure overcomes the critical need to immediately alert potential first responders (e.g., family member(s), co-workers, fitness facility staff, neighbor(s), assisted living facility staff, hotel staff, or any individual with an application on their smart phone or smart device that informs them of a cardiac arrest event and its location) prior to the arrival of professional emergency medical services by detecting that a cardiac arrest has occurred, immediately issuing an audible alarm, and then dialing pre-established phone numbers to alert potential first responders with [a] the individual's name, [b] individual's exact location including GPS-derived latitude and longitude coordinates, [c] time of occurrence of cardiac arrest and, optionally, [d] the location of nearest AED device(s) in the event the nearest AED device(s) is(are) geocoded into a data base accessible by a server. The term "server", as used herein, refers to single-purpose and specially developed computer program(s) and computer hardware operating at a physical location different from the location of the wearable cardiac arrest detection and alerting device and that the server is accessible to wearable cardiac arrest detection and alerting device via cellular telephone communication. The server waits for transmitted data and an alert from a wearable cardiac arrest detection and alerting device or accessory cellular phone and programmable device and, once data and alert are received, responds by utilizing a programmed protocol and accessible data bases to identify and issue a synthesized voice alert to identified first responders including professional emergency medical service providers (e.g., providers accessible via call to 911 in the U.S.).

In addition, an application or applications (hereinafter referred to as an "App" or "Apps") may be installed in the smart phone or other smart device of "first responder" volunteers that could inform them that an individual has suffered a cardiac arrest and the individual's precise location. This process could provide a much broader pool of potential first responders by expanding the set of potential candidates who would be in close proximity to someone who has suffered a cardiac arrest and could provide the most prompt intervention. This would expand smart phone applications (i.e., Apps) from widely used "social media" participation into "social lifesaving" participation. To further enable any potential first responders to provide the most effective level of intervention for an individual suffering a cardiac arrest, AED device(s), whether in the in home of the individual suffering a cardiac arrest or in a nearby location, could be geocoded such that the location of the nearest one or more AED device(s) would be accessible in the server data base. The server would then communicate the location of the nearest known (i.e., geocoded) AED device(s). This would enable a potential first responder who arrives at the location of the individual suffering a cardiac arrest to promptly access the nearest AED device and provide the most effective intervention. In the present disclosure, "first responders" refers to those individuals who can potentially intervene with life saving CPR and/or external defibrillation prior to the arrival of emergency medical services summoned through a telephone call to an emergency phone number (e.g., such as 911 in the U.S.).

BRIEF SUMMARY

The apparatus, system, and method of the present disclosure utilizes a wearable cardiac arrest detection and alerting device that minimizes the probability of a false indication of cardiac arrest by incorporating two or more non-invasive heart function sensing apparatus and methods wherein the apparatus and methods are based on two distinctly different types of heart-function sensing techniques. The apparatus, system, and method of the present disclosure requires that the two or more different types of heart function sensing methods incorporated in the wearable cardiac arrest detection and alerting device detect that the measured heart function parameters (e.g., heart rate, blood flow rate, blood pressure, endogenous electrical signals generated by the heart) using the two or more different types of heart function sensing methods are all below their respective minimum preselected levels indicative of a functioning heart. The requirement that two or more different types of non-invasive heart function measurements must be below predetermined levels to represent the occurrence of cardiac arrest significantly reduces the probability of a false indication of the occurrence of a cardiac arrest in the event that the measured heart function by as many as one of two methods (or two of three methods or three of four methods for heart function measurement) result in a measured heart function parameter that is below a predetermined level due, by way of example, to such factors as movement artifact and/or inadequate contact pressure between the measurement apparatus and the subject's body. The different types of non-invasive heart function sensing apparatus and methods include the measurement of optical, electrical, ultrasound, pressure and/or acoustic signals transmitted into and/or received from human tissue containing one or more blood vessels. The two or more different types of non-invasive heart function sensing apparatus and methods provide transcutaneously measurable parameters (e.g., heart rate, endogenous electrical signal generated within heart, blood pressure, blood flow rate) that can be compared with predetermined minimum values for each heart function sensing apparatus and method to determine if the heart is still functioning or if a cardiac arrest event has occurred. By way of example but without limitation, measurement of the wearer's heart function based on [a] heart-pulse related signals and [b] blood flow rate related signals using two or more different types of non-invasive heart function sensing apparatuses and methods and the requirement that both measured parameters are below predetermined minimum levels increases the probability the detection of the absence of heart function by the wearable detection and alerting device is actually due to the occurrence of a cardiac arrest wherein the heart is no longer achieving effective blood circulation in the individual wearing the device. Although an audible alarm and/or haptic alert will enable subject wearing the wearable cardiac arrest detection and alerting device to manually cancel a false detection of the occurrence of a cardiac arrest event (referred to hereinafter as "false cardiac arrest events"), it is advantageous to the user to avoid frequent false cardiac arrest events and associated alarms due to artifact or adequacy of device contact with the subject wearing the device.

The display on the wearable cardiac arrest detection and alerting device may advantageously include the elapsed time (e.g., display of elapsed minutes and seconds) since the time of detection of a heart function that is below a predetermined lower limit value, i.e., the detected occurrence of a cardiac arrest event. The elapsed time since the detected occurrence of a cardiac arrest event would inform the one or more first responders of the duration since the occurrence of the cardiac arrest event.

The apparatus, system, and method of a first embodiment of the present disclosure for the detection and alerting of first responders in the event of a cardiac arrest is a wearable cardiac arrest detection and alerting device, such as a wristwatch device or bracelet, wherein a first type of non-invasive heart function sensing apparatus and method is based on transcutaneous photoplethysmography and a second type of non-invasive heart function sensing apparatus and method is based on transcutaneous Doppler ultrasound based measurement or laser Doppler based measurement of blood flow rate in tissue. By way of example but without limitation, the apparatus, system, and method of a first embodiment of the present disclosure includes [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis integrated microelectromechanical system (MEMS) accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting device to reduce noise and increase signal-to-noise ratio of signals used to continuously derive an accurate heart rate value, [e] algorithm to continuously analyze measured photon signals to determine whether the measured photon signals are within a predetermined range to confirm that wearable cardiac arrest detection and alerting device is properly functioning and is properly positioned on the individual being monitored and, if measured photon signal levels are within a predetermined range, continuously derive heart rate value, [f] a transducer and receiver to transmit ultrasound signals of a first frequency into tissue and detect reflected ultrasound signals of a second frequency to detect blood flow rate level based on the principle of the velocity-dependent Doppler shift of transmitted and received first and second frequencies, [g] algorithm to continuously analyze measured heart rate value and measured blood flow rate to determine if both measured heart rate and blood flow rate level are below predetermined levels indicative that a cardiac arrest has occurred or is imminent, [h] audible alarm in the event that a cardiac arrest has occurred or is imminent, [i] global positioning satellite (GPS) based receiver or equivalent position locating component to determine latitude and longitude of wearable cardiac arrest detection and alerting device, [j] look-up table in software to determine whether wearable cardiac arrest detection and alerting device is at any of the pre-programmed locations frequented by the individual being monitored by the wearable cardiac arrest detection and alerting device (e.g., locations, such as, for example, individual's home, another home, office, fitness facility, or the like), [k] cellular phone communication component typical of widely used cell phones to place calls in the event a cardiac arrest has occurred or is imminent to a pre-programmed, pre-established list of phone numbers including 911 (for use in the U.S.) or other medical emergency response phone number and any other first responders associated with a pre-programmed locations frequented by the individual being monitored by the wearable cardiac arrest detection and alerting device in the event the wearable cardiac arrest detection and alerting device is determined to be at one of the pre-programmed locations, [l] audible synthesized speech used in issued phone calls to annunciate occurrence of a cardiac arrest, identify the individual's name and specify the exact location of the individual in the form of his or her GPS or equivalent device derived coordinates and, if the individual is at a location with pre-established GPS or equivalent device derived coordinates, the actual address of the individual, and [m] wireless or direct connection to wearable cardiac arrest detection and alerting device from external device (e.g., cell phone) to add look-up table of locations and associated phone numbers corresponding to detected latitude and longitude of wearable cardiac arrest detection and alerting device at time of occurrence of cardiac arrest or imminent cardiac arrest.

By way of example, but without limitation, the apparatus, system, and method of a second embodiment of the present disclosure for the detection of the occurrence of a cardiac arrest and alerting of first responders in the event of a cardiac arrest, incorporating a first optical based heart rate measurement method and a second Doppler ultrasound based method or laser Doppler based method for measuring blood flow rate, is a combination of both [a] a wearable cardiac arrest detection and alerting device, such as a wristwatch device or bracelet and [b] an accessory cellular phone and programmable device maintained within the proximity of the wearable cardiac arrest detection and alerting device (e.g., the cellular phone and programmable device within 10 to 100 meters of wearable cardiac arrest detection and alerting device) during the period of monitoring. The wearable cardiac arrest detection and alerting device of a second embodiment of the present disclosure includes [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting device to reduce noise and increase signal-to-noise ratio of signals used to continuously derive heart rate value, [e] audible alarm in the event that a cardiac arrest has occurred or is imminent and [f] wireless communication hardware and software (e.g., Bluetooth ultra-high frequency transmitter) to transmit heart-rate values to accessory cellular phone and programmable device. The accessory cellular phone and programmable device includes [a] wireless communication hardware and software (e.g., Bluetooth ultra-high frequency transmitter) to receive heart-rate values from the wearable cardiac arrest detection and alerting device [b] algorithm to continuously analyze measured photon signal data received from the wearable cardiac arrest detection and alerting device to determine whether the measured photon signals are within a predetermined range to confirm that wearable cardiac arrest detection and alerting device is properly functioning and is properly positioned on the individual being monitored and, if measured photon signal levels are within a pre-determined range, continuously derive heart rate value, [c] algorithm to continuously analyze measured heart rate values to determine whether a cardiac arrest has occurred or is imminent, [d] audible alarm in the event that a cardiac arrest has occurred or is imminent, [e] global positioning satellite (GPS) based receiver or equivalent position locating component to determine latitude and longitude of wearable cardiac arrest detection and alerting device, [f] look-up table in software to determine whether wearable cardiac arrest detection and alerting device is at any of the pre-programmed locations frequented by the individual being monitored by the wearable cardiac arrest detection and alerting device (e.g., locations such as individual's home, another home, office, fitness facility), [g] cellular phone communication component typical of widely used cell phones with a pre-programmed, pre-established list of phone numbers including 911 (for use in the U.S.) and any first responders associated with a pre-programmed locations frequented by the individual being monitored by the wearable cardiac arrest detection and alerting device in the event the wearable cardiac arrest detection and alerting device is determined to be at one of the pre-programmed locations, and [h] audible synthesized speech to annunciate in placed phone calls the occurrence of a cardiac arrest, identify the individual's name and specify the exact location of the individual in the form of his or her GPS or equivalent device derived coordinates and, if the individual is at a location with pre-established GPS or equivalent device derived coordinates, the actual address of the individual.

By way of example, but without limitation, the apparatus, system, and method of a third embodiment of the present disclosure for the detection of the occurrence of a cardiac arrest and alerting of first responders in the event of a cardiac arrest, incorporating a first optical based heart rate measurement method and a second Doppler ultrasound based method or laser Doppler based method for measuring blood flow rate, includes [a] a wearable cardiac arrest detection and alerting device such as a wristwatch device incorporating cellular communication capability and [b] a server that can receive a cellular phone call from the accessory cellular phone and programmable device enabling the server to immediately identify the phone number(s) of the closest first responders based on the GPS derived location of the subject and immediately issues voice-based phone call alerts to the identified closest first responder(s) as well as to identified emergency medical services associated with the country in which the subject is located (e.g., issuing call to 911 if subject is in the U.S.).

The term "server", as used herein, means a computer program and a machine that waits for an alert via cellular phone communication from a wearable cardiac arrest detection and alerting device or accessory cellular phone and programmable device and responds to the alert according to a pre-programmed set of computer instructions. The pre-programmed set of computer instructions include, by way of example but without limitation, the identification of the phone numbers of the nearest first responder(s) based on the subject's GPS-based location as well as the phone number of the identified emergency medical services associated with the country in which the subject is located (e.g., issuing call to 911 if subject is in the U.S.). The purpose of the server is to share data, hardware and software resources among all subjects using a wearable cardiac arrest detection and alerting device and optional accessory cellular phone and programmable device.

By way of example, but without limitation, the apparatus, system, and method of a fourth embodiment of the present disclosure for the detection of the occurrence of a cardiac arrest and alerting of first responders in the event of a cardiac arrest, incorporating a first optical based heart rate measurement method and a second Doppler ultrasound based method or laser Doppler based method for measuring blood flow rate, includes [a] a wearable cardiac arrest detection and alerting device, such as a wristwatch device or bracelet, [b] an accessory cellular phone and programmable device maintained within the proximity of the wearable cardiac arrest detection and alerting device (e.g., the cellular phone and programmable device within 10 to 100 meters of wearable cardiac arrest detection and alerting device) during the period of monitoring, and [c] a server that can receive a cellular phone call from the accessory cellular phone and programmable device with location of accessory cellular phone and programmable device based on the GPS derived location of the subject enabling the server to immediately identify the phone numbers of the closest first responder(s) and immediately issues voice-based phone call alerts to the identified closest first responder(s), as well as to identified emergency medical services associated with the country in which the subject is located (e.g., issuing call to 911 if subject is in the U.S.).

In other embodiments of the present disclosure, the wearable device transcutaneously measures the blood pressure in place of or in addition to the measurement of heart rate using photoplethysmographic methods or blood flow rate measurement using either a Doppler ultrasound based method or a laser Doppler method for the measurement of blood flow rate to detect the occurrence of a cardiac arrest in the event the blood pressure decreases below a specified minimum pressure level (e.g., 10 mm Hg). In this regard and by way of example, see U.S. patent application Ser. No. 14/395,059 published as U.S. Patent Publication Number US 2015/0335282 on Nov. 26, 2015, the latter reference incorporated herein by reference.

In yet other embodiments of the present disclosure, a three-axis integrated microelectromechanical system (MEMS) accelerometer is used to constantly monitor the movement of the wearable device as a result of natural movements of the wearer (e.g., the wrist supporting the wearable device). In these other embodiments of the present disclosure, the heart function of the wearer is measured only if there is no detectable movement of the wearable device for a predetermined time interval. The state of the wearer in which there is no detectable movement of the wearable device by the three-axis accelerometer is referred to hereinafter as the wearer being "motionless" or the state of "motionlessness". During the predetermined time interval of in which the wearable device is motionless, the most accurate measurements of heart function can be accomplished since there is no motion artifact thereby increasing the signal-to-noise level of the heart function measurement method. In addition to periods during sleep or rest, the state of motionlessness will always occur immediately following the occurrence of a cardiac arrest. Accordingly, it is only necessary to monitor heart function during the state of motionlessness since any detectable movement of the wearable device is inconsistent with the state of cardiac arrest. Advantageously, embodiments in which the heart function of the wearer is measured only if there is no detectable movement of the wearable device for a predetermined time interval also reduce the battery energy storage requirements since measurements are only performed during periods in which the wearable device is motionless.

A rechargeable battery is incorporated in the wearable cardiac arrest detection and alerting device, such as a wristwatch device in the four embodiments of the present disclosure. The rechargeable battery provides the electrical energy required for the various functions performed by the wearable cardiac arrest detection and alerting device for periods of days to weeks between recharging. By way of example, but not limitation, the rechargeable battery may be incorporated into the case of a wristwatch device and/or may be incorporated within the watchband using flexible battery technology or in rigid or flexible form within the links of an expandable watchband.

The digital filtering utilized to minimize signal noise associated with motion artifact may include the use of [a] Moving Average Filtering (in this regard, see Lee, J., et. al., Design of Filter to Reject Motion Artifact of Pulse Oximetry. Comput. Stand. Interfaces 2004; 26: 241-249), [b] Fourier Analysis Filtering (in this regard, see Reddy, K., et. al., Use of Fourier Series Analysis for Motion Artifact Reduction and Data Compression of Photoplethysmographic Signals. IEEE Trans. Instrum. Meas. 2009; 58: 1706-1711), [c] Adaptive Noise Cancellation Filtering using triaxial accelerometer (in this regard, see Asada, H., et. al., Active Noise Cancellation using MEMS accelerometers for Motion-Tolerant Wearable Bio-Sensors. Conf. Proc. IEEE EMBS 2004; 3:2157-2160), [d] Least Mean Square Adaptive Filtering (in this regard, see Wei, P., et. al., A New Wristband Wearable Sensor Using Adaptive Reduction Filter to Reduce Motion Artifact. Proc. of 2008 International Conf. on Information Technology and Applications in BioScience (ITAB, Shenzhen, China). May 2008; 30-31: 278-281 and Ram, M. et. al., A Novel Approach for Artifact Reduction in Photoplethysmographic Signals based on AS-LMS Adaptive Filter. IEEE Instrum, Meas. 2012; 61: 1445-1457), [e] Principal Component Analysis Filtering (in this regard, see Rhee, S., et. al., Artifact-Resistant, Power Efficient Design of Finger-Ring Plethysmographic Sensors. IEEE Trans. Biomed. Eng. 2001; 48: 795-805 and [f] Laguerre Expansion Filtering (in this regard, see Wood, L., et. al., Active Motion Artifact Reduction for Wearable Sensors using Laguerre Expansion and Signal Separation. Proc. IEEE Conference on EMBS Shanghi, China, January 2005; 17-18: 652-655), where all of the above citations are incorporated herein by reference.

Advantageously, in all four embodiments of the present disclosure, a three-axis accelerometer is used to constantly monitor the movement of the wearable device as a result of natural movements of the wearer (e.g., the wrist supporting the wearable device). In these embodiments of the present disclosure, the heart function of the wearer is measured only if there is no detectable movement of the wearable device (i.e., the wearable device is motionless) for a predetermined time interval, $T_1$. During the predetermined time interval of in which the wearable device is motionless, the most accurate measurements of heart function can be accomplished since there is no motion artifact thereby increasing the signal-to-noise level of the heart function measurement method. In addition to periods during sleep or rest, the state of motionlessness will always occur immediately following the occurrence of a cardiac arrest. Accordingly, it is only necessary to monitor heart function during the state of motionlessness since any detectable movement of the wearable device is inconsistent with the state of cardiac arrest. Embodiments in which the heart function of the wearer is measured only if there is no detectable movement of the wearable device for a predetermined time interval reduces the battery energy storage requirements since measurements are only performed during periods in which the wearable device is motionless.

The state of motionlessness (i.e., inactivity) may be detected by continuously monitoring level of acceleration measured using the x-axis, y-axis, and z-axis accelerometers. If the levels of the x-axis, y-axis, and z-axis accelerations measured by all three accelerometers are less than a pre-selected threshold values AccMINx, AccMINy, and AccMINz stored in wearable device for a pre-selected time interval, $T_1$ (e.g., 10 seconds), the wearable device determines that the wearer is in a motionless state. The time interval, $T_1$, during which no movement is detected, may be equal to the time interval, $T_2$, required for the wearable device to obtain an average heart rate value. By way of example, assume that the wearable device heart rate measurement function requires a sampling period of 10.0 seconds in order to obtain a average heart rate value, thereby establishing a value of 10.0 seconds for time interval, $T_2$. Therefore, time interval $T_1$ required to establish that no movement has occurred also is set equal to 10.0 seconds. Alternatively, time interval $T_1$ may be selected to be a time period ranging from 10 to 30 seconds independent of the time to obtain an average heart rate, but time interval $T_1$ must be at least as large as time interval $T_2$ required to obtain a measured value for the heart rate. The detected state of no measurable movement of the wristwatch, also referred to as the state of motionlessness, for $T_1$ seconds, is referred to, in this example, as Level 1 of the cardiac arrest detection sequence and time interval $T_1$ also is referred to as the period of motionlessness. This time interval, $T_1$, during which there was no movement detectable by the three-axis accelerometer, may correspond to a period when [a] the wearer is motionless during sleeping, [b] the wearer is maintaining his or her wrist in a motionless position or [c] the wearer has experienced a cardiac arrest event or reached a motionless state as a result of fainting.

Continuing with this example, upon reaching Level 1, the wearable device obtains a measurement of the wearer's current heart rate, HR, using a first heart function assessment apparatus within time interval $T_1$ of sustained motionlessness and in the absence of movement artifact. The current HR measured within time interval $T_1$ is compared with a preselected minimum heart rate, HRMIN. By way of example, the preselected minimum heart rate value of HRMIN may be 5 to 20 beats/minute. If the current heart rate, HR is less than the minimum heart rate value, HRMIN then a second Level 2 of the cardiac arrest detection sequence is attained.

Continuing with this example, once Level 2 has been attained, a second and different heart function assessment apparatus, system, and method may be employed to determine if a cardiac arrest event has, in fact, occurred. By way of example, laser Doppler blood flow rate measurement would commence upon reaching Level 2 of monitoring heart function of wearer. This stage, at which laser Doppler blood flow rate measurement is immediately commenced, is referred to as Level 3. In this example, the laser Doppler method can be instructed to detect the current relative blood flow rate, BFR2 (in arbitrary units). This detected current relative blood flow rate, BFR2, is compared with the most recent blood flow rate, BFR1 (in arbitrary units) measured during a brief sampling period, BFSP, that occurs at a regular time interval, BFRI. By way of example, the relative blood flow rate measurement can occur during a brief sampling period, BFSP ranging from 2 to 10 seconds that occurs at a regular time interval, BFRI, ranging from 5 to 30 minutes. Hence, the duty cycle for the laser Doppler blood flow rate measurements throughout a 24-hour period may be maintained below 1%, thereby significantly extending the battery life of the wearable device. If the current blood flow rate, BFR2 is more than a preselected blood flow decrement factor, BFDF, below the most recently measured blood flow rate, BFR1 obtained prior to this period and the heart rate is less than the preselected HRMIN, then an audible alarm as well as a vibration (i.e., haptic) alert is issued by the wearable device indicating the suspected occurrence of a cardiac arrest event. By way of example, the preselected blood flow decrement factor, BFDF, may be 3 to 10, preferably at least 5.

In this example case, if the laser Doppler measured blood flow rate obtained in the previous measurement period is 60 arbitrary units and the currently measured blood flow rate is now 10 arbitrary units, then the amount of the measured decrease in the blood flow rate is a factor of 6 which is a greater decrement than the maximum allowed decrement factor of 5 in this example, then an audible alarm as well as a vibration (i.e., haptic) alert would be issued by the wearable device. The wearer can cancel a false alarm by depressing the alarm cancel button located on the wearable device. If the audible alarm and vibration alert are not canceled, then a predefined sequence of steps would be initiated to alert one or more first responders that a cardiac arrest event has been detected.

In the example embodiment described above, the laser Doppler blood flow rate measurement offers the advantages that [a] it is insensitive to the location on the wearer (e.g., the laser diode and photodetector do not need to be positioned over a radial artery in the case of a wristwatch type wearable device) and [b] it is less sensitive to contact pressure between the wearable device and the wearer's skin surface, as compared with pulse-pressure based measurements of heart rate. In addition, the laser Doppler method for measuring blood flow rate provides a very fast response to dynamic changes in the wearer's blood flow rate associated with a cardiac arrest event.

By way of example, but without limitation, the apparatus, system, and method of another embodiment of the present disclosure for the detection of the occurrence of a cardiac arrest and alerting of first responders in the event of a cardiac arrest, may measure mechanical pressure exerted by pulse in radial artery rather than laser Doppler measured blood flow rate. In this regard, see Wriskwatch wearable device offered by Emergency Medical Technologies, North Miami Beach, Fla.

By way of example, but without limitation, the apparatus, system, and method of yet another embodiment of the present disclosure for the detection of the occurrence of a cardiac arrest and alerting of first responders in the event of a cardiac arrest, may measure pulse-induced movement of vessel wall in radial artery using Doppler Ultrasound method rather than laser Doppler measured blood flow rate. In this regard, see U.S. Pat. Nos. 6,843,771 and 7,798,970, incorporated herein in their entirety by reference.

A significant advantage of the embodiments incorporating a multi-level detection approach is that the only components that are operating continuously are [a] the three-axis accelerometer that monitors whether the wristwatch has been completely stationary for a period of at least $T_1$ seconds and [b] the heart rate apparatus and method performed during a period of motionlessness and in the absence of motion artifact. This approach conserves battery power and enables the assessment of heart function using more sensitive apparatus, system and method (such as the laser Doppler apparatus and method) [a] only during periods in which a first heart function assessment indicates the possibility of the occurrence of a cardiac arrest event and [b] only during a period of motionlessness of the wearable device and likewise in the absence of any motion artifact.

The GPS receiver based positioning component relies on electromagnetic wave communication with satellites that orbit the Earth. To determine the exact location of the individual that encounters a cardiac arrest, the GPS receiver within the wearable cardiac arrest detection and alerting device (e.g., wrist watch) or accessory cellular phone and programmable device (typically located within a distance of 10 to 100 meters from the wearable cardiac arrest detection and alerting device) determines the locations of at least three satellites out of a world-wide total of about 24 orbiting satellites above the GPS receiver. The GPS receiver then uses three-dimensional trilateration to determine the exact location of the GPS receiver by mathematically constructing a sphere around each of three satellites that the GPS receiver locates. These three spheres geometrically intersect in two points—one in space, and one on the ground. The point on the ground at which the three spheres geometrically intersect is the exact location of the GPS receiver expressed in units of latitude and longitude on the earth's surface.

The apparatus, system, and method of the present disclosure utilize latitude and longitude coordinate information in two important ways. First, if a location is known in terms of a street address and postal code (e.g., an individuals residence location), the location can be converted into an equivalent set of latitude and longitude coordinates using forward geocoding. For example, one method of forward geocoding is address interpolation. This method makes use of data from a street geographic information system where the street network is already mapped within the geographic coordinate space. Each street segment is attributed with address ranges (e.g., house numbers from one segment to the next). Geocoding takes an address, matches it to a street and specific segment (such as a block, in towns that use the "block" convention). Geocoding then interpolates the position of the address, within the range along the segment, to derive the latitude and longitude coordinates for a specified address. Second, reverse geocoding is utilized to obtain the back (reverse) coding of a point location (latitude and longitude coordinates) into a readable address and place name (if also known). This permits the identification of nearest street address and location name (e.g., hotel name). Utilizing internet-based geocoding services, reverse geocoding enables the conversion of the latitude and longitude coordinates obtained by the GPS component into a readable street address that can be communicated to one or more first responders according to the teachings of the present disclosure. By way of example, GeoNames provides a reverse geocoding web service that is capable of identifying the nearest street address (and place names, if known) from the GPS-derived latitude and longitude coordinates.

The physical addresses and associated phone numbers (e.g., neighbor's phone numbers) of individual's frequented locations or in close proximity to individual's frequented locations (e.g., home address, office address, fitness facility address, hotel(s), airport(s), business addresses) are converted to latitude and longitude coordinates using forward geocoding software available on the internet. The derived latitude and longitude coordinates corresponding to the street addresses and phone numbers are used by wearable cardiac arrest detection and alerting device, accessory cellular phone and programmable device or server to call the phone numbers of identified first responders at the detected address that cardiac arrest occurred as well as to call an emergency medical service (e.g., by placing call to 911 in the U.S.). All issued phone calls include synthesized voice specification of the name of individual experiencing a cardiac arrest and his or her current address. The language used by the voice synthesizer is based on the GPS-derived country in which the wearable cardiac arrest detection and alerting device is located at the time that the individual experiences a cardiac arrest. By way of example, the languages may include, for example, English, Mandarin, Spanish, French, German, Dutch, Italian, Portuguese, Danish, Norwegian, Swedish, Finnish, Russian, Polish, Hungarian, Hindi, Bengali, Javanese, Greek, Arabic, Persian, Japanese, Korean, Vietnamese, and Turkish.

In the event the individual experiencing a cardiac arrest is not at one of the pre-programmed locations and associated phone numbers, the wearable cardiac arrest detection and alerting device, accessory cellular phone and programmable device or server accesses the internet to utilize reverse geocoding thereby converting GPS-derived latitude and longitude coordinates of wearable cardiac arrest detection and alerting device to the nearest physical street address. Once the nearest street address is identified using reverse geocoding, then the wearable cardiac arrest detection and alerting device, accessory cellular phone and programmable device or server accesses the internet to identify phone numbers associated with identified street address. One or more telephone calls are next issued (i.e., in addition to phone call to emergency medical services at, for example 911) to the identified phone number(s) of one or more nearby first responders to alert the one or more first responders that individual at or adjacent to their location has just experienced a cardiac arrest and immediate action is required (e.g., main desk at hotel or restaurant, main number of workplace, front desk of fitness facility, main number of department store or airport).

In addition, an application or applications (hereinafter referred to as an "App" or "Apps") may be installed in the smart phone or other smart device of "first responder" volunteers that could inform them that an individual has suffered a cardiac arrest and the individual's precise location. This process could provide a much broader pool of potential first responders by expanding the set of potential candidates who would be in close proximity to someone who has suffered a cardiac arrest and could provide the most prompt intervention. This would expand smart phone applications (i.e., Apps) from widely used "social media" participation into "social lifesaving" participation. To further enable any potential first responders to provide the most effective level of intervention for an individual suffering a cardiac arrest, AED device(s), whether in the in home of the individual suffering a cardiac arrest or in a nearby location, could be geocoded such that the location of the nearest one or more AED device(s) would be accessible in the server data base. The server would then communicate the location of the nearest known (i.e., geocoded) AED device(s). This would enable a potential first responder who arrives at the location of the individual suffering a cardiac arrest to access the nearest AED device and provide the most effective intervention.

The audible alarm is combined with synthesized speech to alert first responder that cardiac arrest has occurred and that cardiopulmonary resuscitation (CPR) and external defibrillation, if available, needs to commence immediately. By way of example, but without limitation, upon the detected occurrence of cardiac arrest, the audible alarm emits a tone at a loudness level of, say, 90 decibels at a single or varying frequency interrupted every five seconds to annunciate verbal alert that cardiac arrest has occurred and that (CPR) and external defibrillation (if available) needs to commence immediately.

A detection apparatus, system, and method are also incorporated in the wearable cardiac arrest detection and alerting device, such as a wristwatch type device, in all four embodiments of the present disclosure in order to assure that the wearable cardiac arrest detection and alerting device is in sufficient contact with the individual wearer's body to enable heart function measurement. By way of example and without limitation, the detection apparatus, system and method may employ one or more of the following methods including [1] sensing of body heat based on direct temperature sensing or indirect infrared temperature sensing, [2] measurement of electrical conductance or impedance of the subject's skin layer adjacent to and in contact with wearable cardiac arrest detection and alerting device, [3] measurement of electrical capacitance of subject's body adjacent to and in contact with wearable cardiac arrest detection and alerting device, and/or [4] mechanical switch, pneumatic switch (e.g., dome switch) or pressure transducer. One or more detection apparatus, systems and methods and associated measured parameters are compared with pre-determined values to determine whether the contact between the wearable cardiac arrest detection and alerting device and the surface individual's body (e.g., wrist) is sufficient to enable reliable heart function measurement.

Also, in order to further minimize the possibility of issuing a false alarm to first responders, the wearable cardiac arrest detection and alerting device and/or accessory cellular phone and programmable device of the present disclosure will issue an audible alert in the immediate surroundings of the subject, as well as a vibration (i.e., haptic) alert, for a period sufficiently long to enable subject to cancel any false detection of a cardiac arrest prior to the broadcast of an alarm to first responders. By way of example, a distinct 90 dB audible tone would be issued by the wearable cardiac arrest detection and alerting device and/or accessory cellular phone and programmable device for a period of 15 to 30 seconds to enable subject to cancel a false alarm before the apparatus and system of the present disclosure broadcasts the detected occurrence of a cardiac arrest to first responders. A "cancel alarm" function would be incorporated in the wearable cardiac arrest detection and alerting device (i.e., device that is being worn or intended to be worn) and/or in the accessory cellular phone and programmable device so that the subject can prevent the broadcast of any false alarm. By way of example, a false alarm may be caused by wrist-worn wearable cardiac arrest detection and alerting device losing adequate contact with skin surface to enable measurement of the heart function or the interface between the wearable cardiac arrest detection and alerting device and the subject becoming sufficiently wet to affect the heart function measurement.

Once the first responders arrive at the location of the individual that is in a state of cardiac arrest, CPR and/or defibrillation using an AED, if readily accessible, would promptly commence while awaiting the arrival of trained emergency medical personnel alerted via the automated 911 call and GPS-based locator for the individual that is in a state of cardiac arrest.

In yet another embodiment of the present disclosure, the wearable cardiac arrest detection and alerting device may be worn at some other location on the human body, by way of example, around the torso, around the upper arm, on a finger in a form similar to a ring or around the head in the form of a head band mounted device.

Other objects of the disclosure will, in part, be obvious and will, in part, appear hereinafter. The disclosure, accordingly, includes the apparatus, system and method possessing the construction, combination of elements, arrangement of parts and steps, which are exemplified in the following detailed description.

BRIEF DESCRIPTION OF THE DRAWINGS

For a fuller understanding of the nature and advantages of the present method and process, reference should be had to the following detailed description taken in connection with the accompanying drawings, in which:

FIG. 6 is a pictorial representation of a top view of the system comprising a wearable cardiac arrest detection and alerting device and accessory cellular phone and programmable device in a second embodiment of the present disclosure;

FIGS. 11A and 11B combine as labeled thereon to provide a flow chart describing the operation and use of the wearable cardiac arrest detection and alerting device of another preferred embodiment of the present disclosure as seen in FIGS. 1-4 and 8 wherein heart function measurements commence only when wearable device is motionless.

The drawings will be described in further detail below.

DETAILED DESCRIPTION

Figure 2:
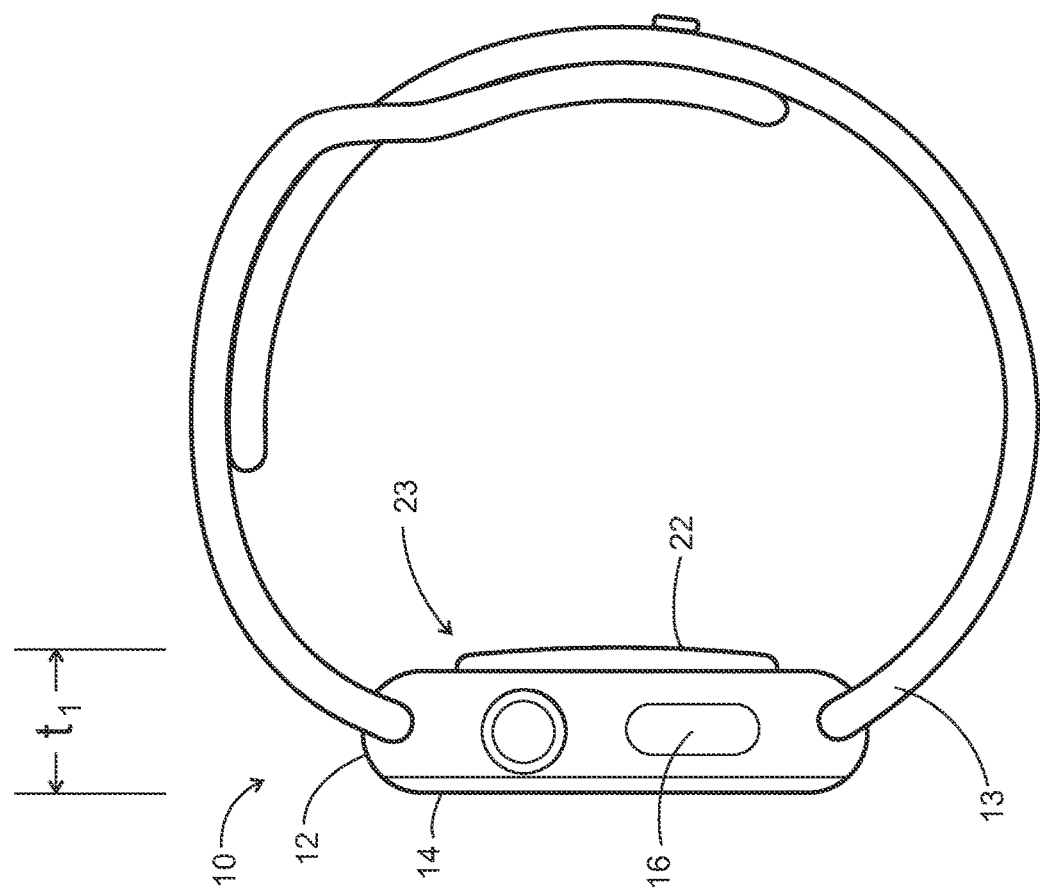
FIG. 2 is a pictorial representation of a side view of the wearable cardiac arrest detection and alerting device for all four embodiments of the present disclosure.
Figure 1:
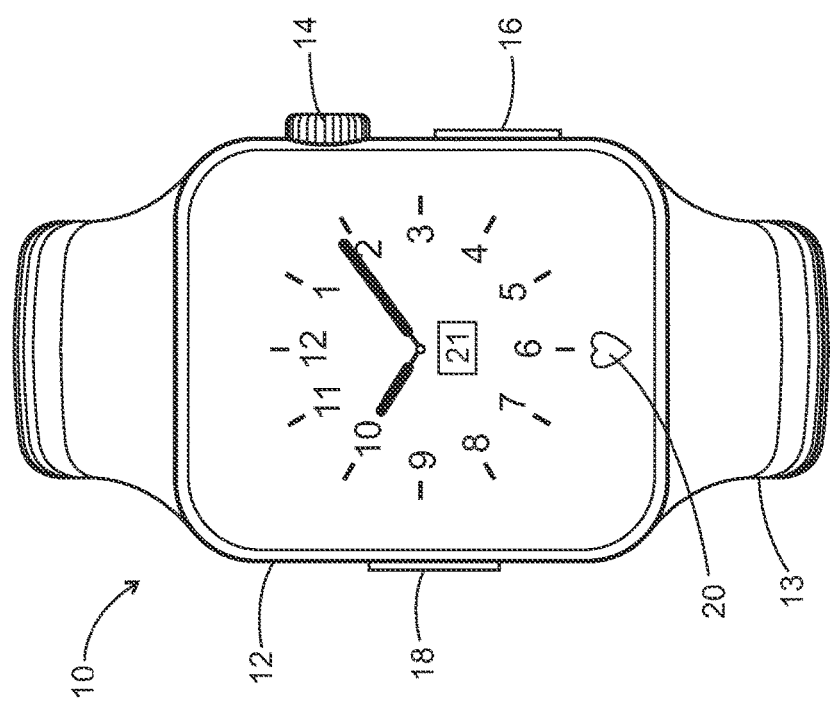
FIG. 1 is a pictorial representation of a top view of the wearable cardiac arrest detection and alerting device for all four embodiments of the present disclosure.

In the disclosure to follow, initially seen in FIGS. 1 and 2 representing all four embodiments of the present disclosure for the detection and alerting of first responders in the event of a cardiac arrest or imminent cardiac arrest. As seen in the exterior front surface view of a wearable cardiac arrest detection and alerting device, 10, in FIG. 1, wearable cardiac arrest detection and alerting device 10 includes a case, 12, a wrist-band, 13, a clock adjustment stem, 14, an on/off toggle switch for heart rate monitor, 16, a display toggle switch, 18, a heart icon, 20, displayed when heart rate monitoring function is active, and a clock display, 21. As seen in the exterior side view of wearable cardiac arrest detection and alerting device 10 in FIG. 2, a back surface, 23, of wearable cardiac arrest detection and alerting device 10 includes a sensor support member, 22, and sensor, as well as battery charging components (not shown in FIG. 2).

Still referring to FIGS. 1 and 2, wearable cardiac arrest detection and alerting device 10 includes a number of internal components (not seen in FIGS. 1 and 2) including by way of example, but not limited to, [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting to reduce noise and increase signal-to-noise ratio of signals used to continuously derive heart rate value, [e] algorithm to continuously analyze measured photon signals to determine whether the measured photon signals are within a predetermined range to confirm that wearable cardiac arrest detection and alerting is properly functioning and is properly positioned on the individual being monitored and, if measured photon signal levels are within a pre-determined range, continuously derive heart rate value, [f] ultrasound transmitter and receiver to enable Doppler ultrasound-based measurement of blood flow rate or laser diode and photo-detector to enable laser Doppler-based measurement of blood flow rate, [g] algorithm to continuously analyze measured heart rate values and measured blood flow rate values to determine whether both are below predetermined levels indicative that a cardiac arrest has occurred or is imminent, [h] actuatable audible alarm, as well as a vibration (i.e., haptic) alert, in the event that a cardiac arrest has occurred or is imminent, [i] global positioning satellite (GPS) based receiver or equivalent position locating component to determine latitude and longitude of wearable cardiac arrest detection and alerting, [j] look-up table in software to determine whether wearable cardiac arrest detection and alerting is at any of the pre-programmed locations frequented by the individual being monitored by the wearable cardiac arrest detection and alerting (e.g., locations such as individual's home, another home, office, fitness facility), [k] cellular phone communication component typical of widely used cell phones to place calls in the event a cardiac arrest has occurred or is imminent to a pre-programmed, pre-established list of phone numbers including 911 (for use in the U.S.) or other medical emergency response phone number and any other first responders associated with a pre-programmed locations frequented by the individual being monitored by the wearable cardiac arrest detection and alerting in the event the wearable cardiac arrest detection and alerting is determined to be at one of the pre-programmed locations, and [l] audible synthesized speech for use in placed phone calls to annunciate occurrence of a cardiac arrest, identify the individual's name and specify the exact location of the individual in the form of his or her GPS or equivalent device derived coordinates and, if the individual is at a location with pre-established GPS or equivalent device derived coordinates, the actual address of the individual. By way of example but without limitation, the accelerometer referred to in the embodiments of this disclosure may be an integrated microelectromechanical system (MEMS) such as the Model No. ADXL345 manufactured by Analog Devices, Norwood, Mass. In this regard, see Jia N., Detecting Human Falls with a 3-Axis Digital Accelerometer. Analog Dialogue 2009; 43(07): 1-6.

Figure 3:
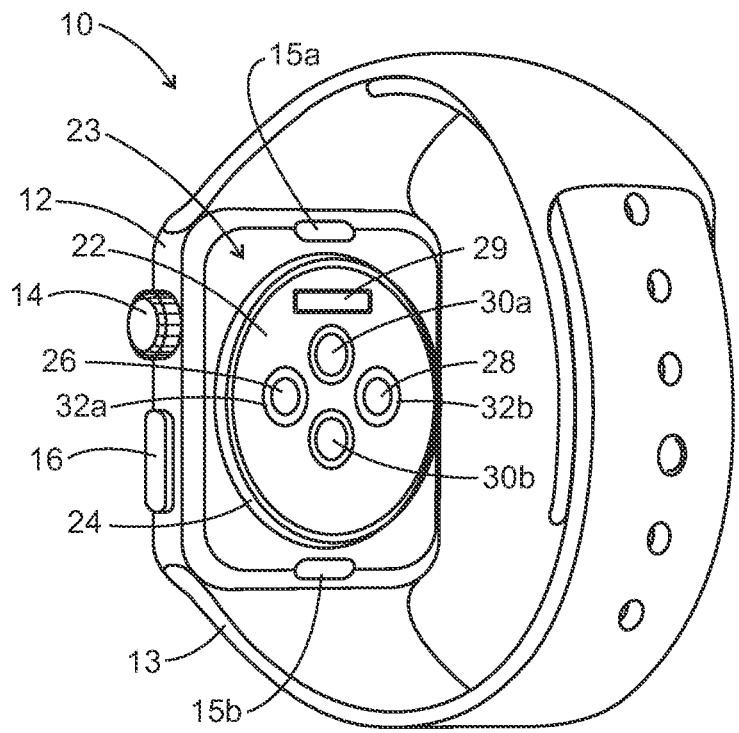
FIG. 3 is an isometric pictorial representation of a back view of the wearable cardiac arrest detection and alerting device for all four embodiments of the present disclosure showing Photoplethysmographic and Doppler ultrasound based heart-function measuring sensors and magnetic coupling components.

Referring now to FIG. 3, a perspective view of back surface 23 of wearable cardiac arrest detection and alerting device 10 is seen, which includes wrist band release springs, 15a and 15b, a sensor support member, 22, a water-proof sealing gasket, 24, a photon source, 26, of first wavelength Lambda1, a photon source, 28, of second wavelength Lambda2, electro-optical photodetectors, 30a, and 30b, and battery charging terminals, 32a and 32b, for coupling to inductive battery charging pod (not shown in FIG. 3) and ultrasound transmitter and receiver 29 to enable Doppler ultrasound based transcutaneous measurement of blood flow rate. Photon sources 26 and 28 preferably are light emitting diode (LED) components due to their small size and capability to be cyclically energized for very brief periods for energized durations on the order of microseconds to milliseconds. The operating frequency of the ultrasound transmitter and receiver 29 is preferably in the range from 2 MHz to 20 MHz. Also, the ultrasound transmitter and receiver 29 may alternatively be placed on watchband rather than back surface 23 of wearable cardiac arrest detection and alerting device 10.

First wavelength Lambda1 may be in the visible red spectrum between 600 nanometers (nm) and 760 nanometers (nm) and second wavelength Lambda2 may be in the infrared spectrum between 800 nm and 950 nm. Alternatively, first wavelength Lambda1 may be in the visible green spectrum with a wavelength of 560 nm and second wavelength Lambda2 may be in the visible green spectrum with a wavelength of 577 nm. The two wavelengths in the visible green spectrum are used since the biggest difference in hemoglobin extinction coefficients between deoxyhemoglobin, RHb, and oxyhemoglobin, $HbO_2$, occur at these two green wavelengths (in this regard, see U.S. Pat. No. 5,830,137, incorporated herein by reference).

Figure 4:
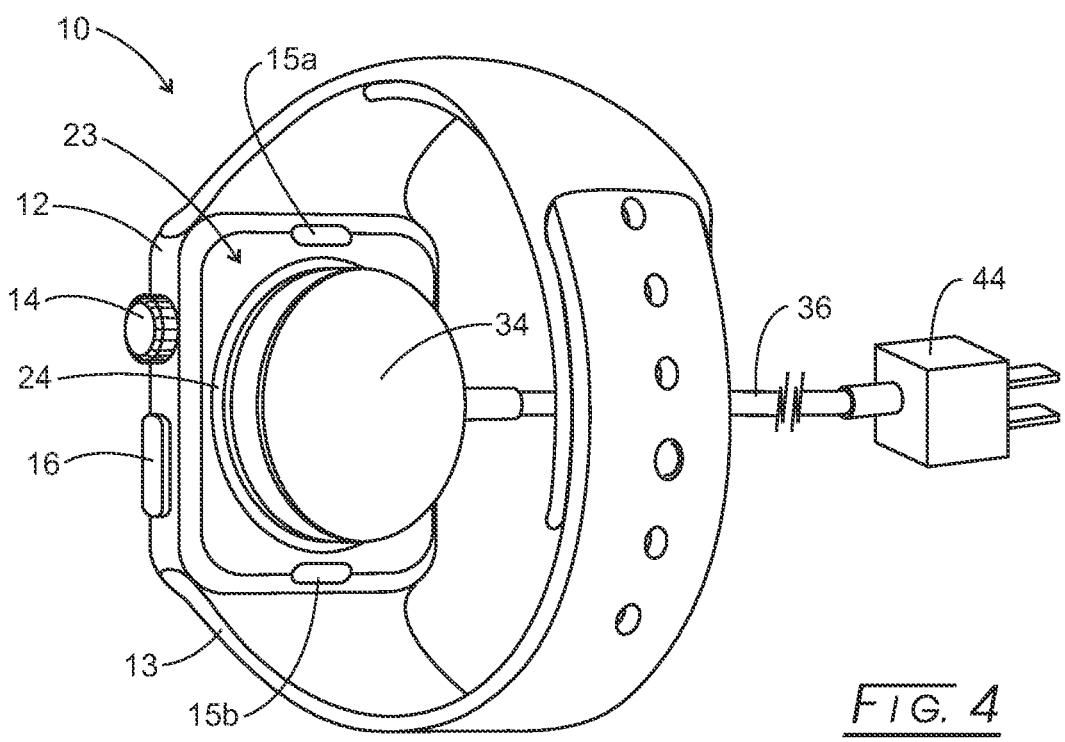
FIG. 4 is an isometric pictorial representation of a back view of the wearable cardiac arrest detection and alerting device for all four embodiments of the present disclosure showing the recharging module positioned over the backside of a wristwatch styled device.

Referring now to FIG. 4, a perspective view of back surface 23 of wearable cardiac arrest detection and alerting device 10 is seen in combination with an inductive battery charging pod, 34, a charging pod cable, 36, and a power source, 44, for inductive battery charging pod 34. Battery charging terminals 32a and 32b seen in FIG. 3 for coupling to inductive battery charging pod 34 may advantageously incorporate a ferromagnetic metal to enable magnetic coupling, optimum alignment and securing of inductive battery charging pod 34 in position adjacent to battery charging terminals 32a and 32b. The magnetic coupling may be achieved with inductive battery charging pod 34 by incorporating one or more permanent magnets within inductive battery charging pod 34 (not seen in FIG. 4), such as, for example, disc shaped neodymium-iron-boron magnets having a diameter ranging from 0.12" to 0.37" and thickness ranging from 0.06" to 0.20".

Figure 5:
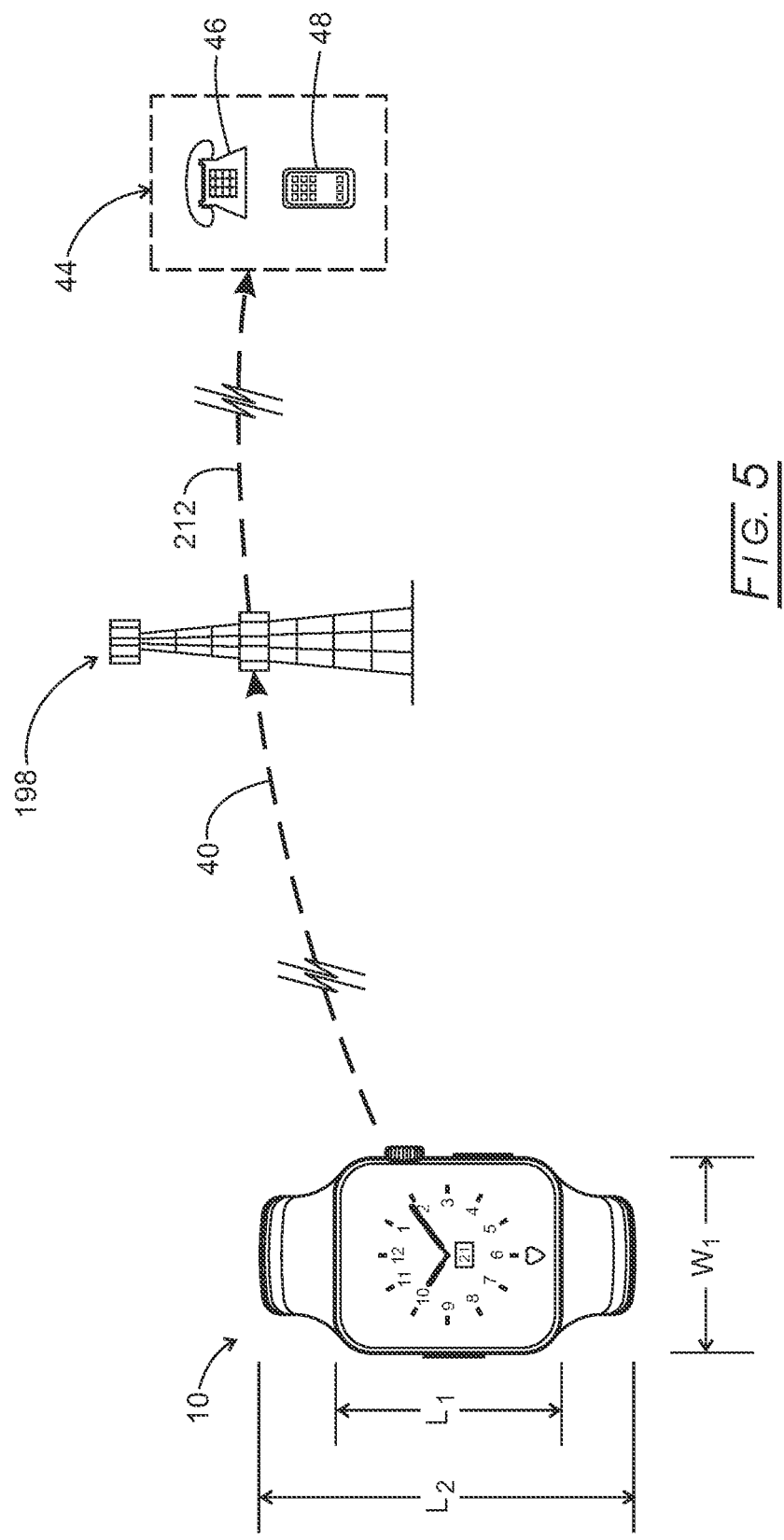
FIG. 5 is a pictorial representation of a top view of the system comprising a wearable cardiac arrest detection and alerting device and server in a first embodiment of the present disclosure.

A pictorial representation of the apparatus and system of a first embodiment of the present disclosure is presented in FIG. 5 for the detection and alerting of first responders in the event of a cardiac arrest the apparatus. As seen in FIG. 5, the first embodiment includes wearable cardiac arrest detection and alerting device 10, where the wearable cardiac arrest detection and alerting device 10 is in wireless communication, 40, to a cellular receiving/transmitting tower, 198. Wearable cardiac arrest detection and alerting device 10 includes a number of internal components (not seen in FIGS. 1, 2, and 5) including by way of example, but not limited to, [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting to reduce noise and increase signal-to-noise ratio of signals used to continuously derive heart rate value, [e] actuatable audible alarm as well as a vibration (i.e., haptic) alert in the event that a cardiac arrest has occurred or is imminent, [f] ultrasound transmitter and receiver to enable Doppler ultrasound-based measurement or laser diode and photodetector to enable laser Doppler-based measurement of blood flow rate, [g] algorithm to continuously analyze measured heart rate values and measured blood flow rate values to determine whether both are below predetermined levels indicative that a cardiac arrest has occurred or is imminent, [h] one or more sensors to confirm the wearable cardiac arrest detection and alerting is in contact with subjects skin and accessible to source of detectable heart beat (e.g., transcutaneous electrical sensor measuring electrical impedance of skin), [i] wireless communication hardware and software, [h] programmed subject name and/or unique identification (e.g., wearable cardiac arrest detection and alerting device phone number), [j] recharging and programming port (e.g., port to enter subject name or other unique identification), [k] GPS-based component to determine latitude and longitude coordinates of wearable cardiac arrest detection and alerting device, [l] display capable of indicating time, heart rate and warning messages regarding adequate contact with subject to enable detection of true heart function and battery level, [n] on/off button to cancel alarm in the event of a false detection of a cardiac arrest, and [o] audible synthesized speech to annunciate in subsequent placed phone calls that a cardiac arrest has occurred, identify the individual's name and specify the exact location of the individual in the form of his or her GPS or equivalent device derived coordinates and, if the individual is at a location with pre-established GPS or equivalent device derived coordinates, the actual address of the individual. Wearable cardiac arrest detection and alerting device 10 incorporates a software-based look-up table, as well as access to internet-based phone numbers using reverse geocoding to identify locations and associated phone numbers of first responders corresponding to the GPS-detected latitude and longitude of wearable cardiac arrest detection and alerting at time of occurrence of cardiac arrest or imminent cardiac arrest. The communication of an alert in the event of a cardiac arrest to one or more telephone(s) 46, and/or cellular phone(s), 48, at locations represented by block 44 of first responders is issued from a cellular receiving/transmitting tower, 198, via a wireless communication path, 212.

By way of example, but without limitation, the apparatus and system of a second embodiment of the present disclosure for the detection and alerting of first responders in the event of a cardiac arrest is illustrated pictorially in FIG. 6. As seen in FIG. 6, the apparatus and system of a second embodiment of the present disclosure includes a combination of both [a] wearable cardiac arrest detection and alerting device 10 and [b] accessory cellular phone and programmable device 39 maintained within the proximity of the wearable cardiac arrest detection and alerting device (e.g., cellular phone and programmable device 39 within 10 to 100 meters of wearable cardiac arrest detection and alerting device 10) during the period of monitoring. Wearable cardiac arrest detection and alerting device 10 includes a number of internal components (not seen in FIGS. 1, 2, and 6) including by way of example, but not limited to, [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting device to reduce noise and increase signal-to-noise ratio of signals used to continuously derive heart function value, [e] actuatable audible alarm as well as a vibration (i.e., haptic) alert in the event that a cardiac arrest has occurred or is imminent, [f] one or more sensors to confirm the wearable cardiac arrest detection and alerting device is in contact with subjects skin and accessible to source of detectable heart beat (e.g., transcutaneous electrical sensor measuring electrical impedance of skin), and [g] wireless communication hardware and software (e.g., Bluetooth ultra-high frequency transmitter) to transmit heart-rate values to accessory cellular phone and programmable device 39.

Still referring to FIG. 6, accessory cellular phone and programmable device 39 includes [a] wireless communication hardware and software (e.g., Bluetooth ultra-high frequency transmitter) to receive heart-rate values from the wearable cardiac arrest detection and alerting device [b] algorithm to continuously analyze measured photon signal data received from the wearable cardiac arrest detection and alerting device to determine whether the measured photon signals are within a predetermined range to confirm that wearable cardiac arrest detection and alerting device is properly functioning and is properly positioned on the individual being monitored and, if measured photon signal levels are within a pre-determined range, continuously derive heart rate value, [c] ultrasound transmitter and receiver to enable Doppler ultrasound-based measurement or laser diode and photodetector to enable laser Doppler-based measurement of blood flow rate, [d] algorithm to continuously analyze measured heart rate values and measured blood flow rate values to determine whether both are below predetermined levels indicative that a cardiac arrest has occurred or is imminent, [e] actuatable audible alarm as well as a vibration haptic) alert in the event that a cardiac arrest has occurred or is imminent, [f] global positioning satellite (GPS) based receiver or equivalent position locating component to determine latitude and longitude of wearable cardiac arrest detection and alerting device, [g] look-up table in created software to determine whether wearable cardiac arrest detection and alerting device is at any of the pre-programmed locations frequented by the individual being monitored by the wearable cardiac arrest detection and alerting device (e.g., locations such as individual's home, another home, office, fitness facility), [h] cellular phone communication component typical of widely used cell phones with a pre-programmed, pre-established list of phone numbers including 911 (for use in the U.S.) and any first responders associated with a pre-programmed locations frequented by the individual being monitored by the wearable cardiac arrest detection and alerting device in the event the wearable cardiac arrest detection and alerting device is determined to be at one of the pre-programmed locations, and [i] audible synthesized speech to annunciate in placed phone calls that a cardiac arrest has occurred, identify the individual's name and specify the exact location of the individual in the form of his or her GPS or equivalent device derived coordinates and, if the individual is at a location with pre-established GPS or equivalent device derived coordinates, the actual address of the individual. The communication of an alert in the event of a cardiac arrest to one or more telephone(s) 46 and/or cellular phone(s) 48 at one or more locations represented by block 44 of first responders is issued first from accessory cellular phone and programmable device 39 to cellular receiving/transmitting tower 198 via wireless communication path 214 and then from cellular receiving/transmitting tower 198 to one or more telephone(s) 46 and/or one or more cellular phones 48 via wireless communication path 216.

Figure 8:
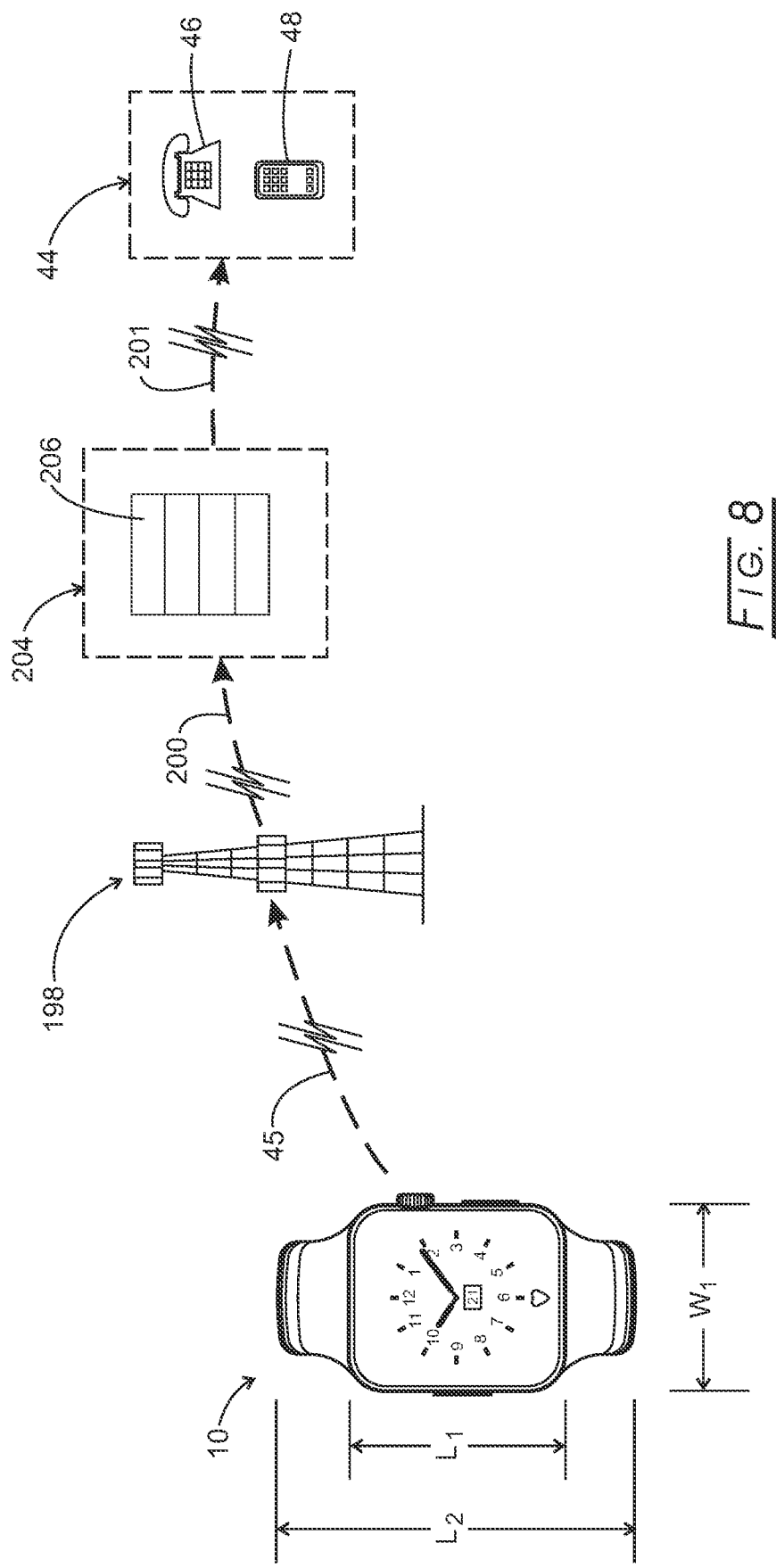
FIG. 8 is a pictorial representation of a top view of the system comprising a wearable cardiac arrest detection and alerting device, server and land-line based telephone and/or cellular phone of one or more first responders in a third and preferred embodiment of the present disclosure.

By way of example, but without limitation, the apparatus, system, and method of a third and preferred embodiment of the present disclosure is shown in FIG. 8 for the detection and alerting of first responders in the event of a cardiac arrest and includes [a] wearable cardiac arrest detection and alerting device 10 such as a wristwatch device incorporating cellular communication capability and [b] a server 206 at some other physical location represented by block 204 that can receive a cellular phone call from the wearable cardiac arrest detection and alerting device 10 enabling the server 206 to immediately identify the phone number(s) of the closest first responders based on the GPS derived location of the subject and immediately issues voice-based phone call alerts to the identified closest first responder(s) as well as to identified emergency medical services associated with the country in which the subject is located (e.g., issuing call to 911 if subject is in the U.S.). As seen in FIG. 8, the apparatus and system of a third embodiment of the present disclosure includes, by way of example, a combination of both [a] a wearable cardiac arrest detection and alerting device 10 and [b] a server, 206, at some other physical location represented by block 204. Wearable cardiac arrest detection and alerting device 10 includes a number of internal components (not seen in FIGS. 1, 2, and 8) including by way of example, but not limited to, [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting device to reduce noise and increase signal-to-noise ratio of signals used to continuously derive heart rate value, [e] actuatable audible alarm as well as a vibration (i.e., haptic) alert in the event that a cardiac arrest has occurred or is imminent, [f] one or more sensors to confirm the wearable cardiac arrest detection and alerting device is in contact with subjects skin and accessible to source of detectable heart beat (e.g., transcutaneous electrical sensor measuring electrical impedance of skin), [g] recharging and programming port (e.g., port to enter subject name or other unique identification), [h] GPS-based component to determine latitude and longitude coordinates of wearable cardiac arrest detection and alerting device, [k] display capable of indicating time, heart rate and warning messages regarding adequate contact with subject to enable detection of true heart rate and battery level, [i] on/off button to cancel alarm in the event of a false detection of a cardiac arrest, and [j] wireless communication hardware and software to transmit the GPS location and an alert related to the occurrence of a cardiac arrest by the subject being monitoring by wearable cardiac arrest detection and alerting device 10.

Figure 9:
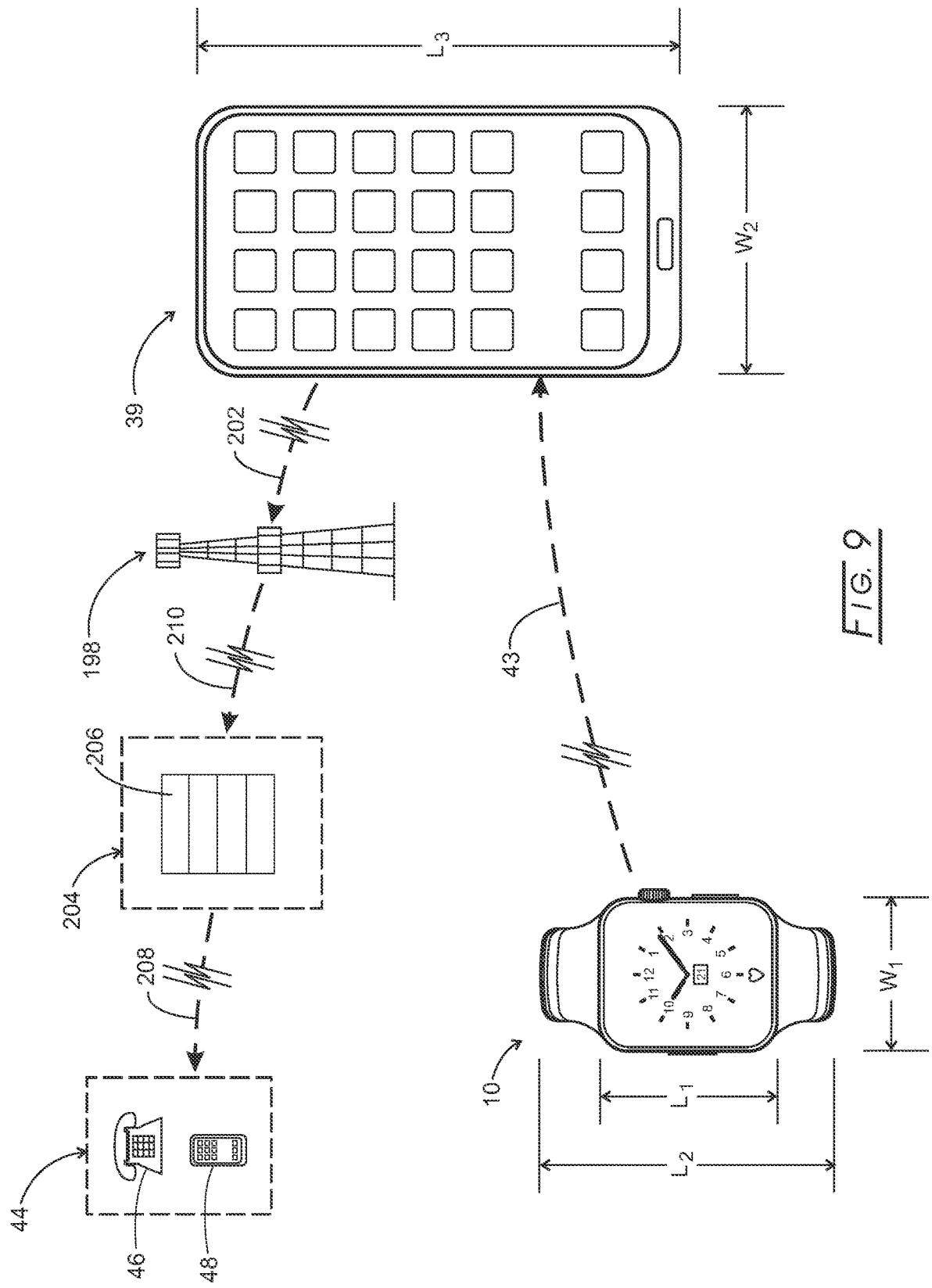
FIG. 9 is a pictorial representation of a top view of the system comprising a wearable cardiac arrest detection and alerting device, server and land-line based telephone and/or cellular phone of one or more first responders and accessory cellular phone and programmable device in a fourth embodiment of the present disclosure.

Still referring to FIG. 8, server 206 located at some other physical location represented by block 204 includes [a] wired or wireless communication hardware and software to receive subject's GPS location and from the wearable cardiac arrest detection and alerting device via wireless communication path 200 [b] look-up table in software to determine whether wearable cardiac arrest detection and alerting device is at any of the pre-programmed locations frequented by the particular individual being monitored by the wearable cardiac arrest detection and alerting device (e.g., locations such as individual's home, another home, office, fitness facility), [c] access to reverse geocoding data base to identify nearest phone numbers of potential first responders based on subject's GPS-derived location in the event the subject is not at one the frequented pre-programmed locations, [d] cellular phone communication component to call identified phone numbers of first responders identified above in [b] or [c] either the pre-programmed phone numbers if the subject is confirmed by reverse-geocoding to be at one of the including 911 (for use in the U.S.), and [e] audible synthesized speech to annunciate in placed phone calls that a cardiac arrest has occurred, identify the individual's name and specify the exact location of the individual in the form of subject's GPS location or equivalent device derived coordinates and, using reverse geocoding data base software, the actual address of the individual. The communication of an alert in the event of a cardiac arrest to the one or more telephone(s) 46 and/or cellular phone(s) 48 at one or more locations signified by block 44 of first responders is issued first from wearable cardiac arrest detection and alerting device 10 to a cellular receiving/transmitting tower 198 via wireless communication path 45 and then from cellular receiving/transmitting tower 198 to server 206 via wireless communication path 200. The communication of an alert in the event of a cardiac arrest proceeds from server 206 via wired and/or a wireless path, 201, to one or more telephone(s) 46 and/or cellular phone(s) 48 at one or more locations represented by block 44. By way of example, but without limitation, the apparatus and system of a fourth embodiment of the present disclosure for the detection and alerting of first responders in the event of a cardiac arrest is illustrated pictorially in FIG. 9. As seen in FIG. 9, the apparatus and system of a fourth embodiment of the present disclosure includes [a] wearable cardiac arrest detection and alerting device 10, [b] accessory cellular phone and programmable device 39 maintained within the proximity of the wearable cardiac arrest detection and alerting device (e.g., cellular phone and programmable device 39 within 10 to 100 meters of wearable cardiac arrest detection and alerting device 10) during the period of monitoring and [c] server 206 at some other physical location represented by block 204. Server 206 is capable of receiving a cellular phone call from accessory cellular phone and programmable device 39 enabling server 206 to immediately identify the phone number(s) of the closest first responders based on the GPS derived location of the subject and immediately issues voice-based phone call alerts to the identified closest first responder(s) as well as to identified emergency medical services associated with the country in which the subject is located (e.g., issuing call to 911 if subject is in the U.S.). Wearable cardiac arrest detection and alerting device 10 includes a number of internal components (not seen in FIGS. 1, 2 and 9) including by way of example, but not limited to, [a] one or more photon sources incorporating one or more electromagnetic energy wavelengths used to continuously or intermittently transmit electromagnetic energy transcutaneously into tissue containing one or more blood vessels, [b] one or more photon detectors to continuously and transcutaneously measure photon signal levels associated with transmitted photons, [c] three-axis accelerometer to generate electrical signal levels corresponding to movement of wearable cardiac arrest detection and alerting device, [d] signal processing hardware componentry and software using photon detector measured electrical signals and accelerometer generated electrical signals to digitally filter artifact caused by movement of the wearable cardiac arrest detection and alerting device to reduce noise and increase signal-to-noise ratio of signals used to continuously derive heart rate value, [e] ultrasound transmitter and receiver to enable Doppler ultrasound-based measurement or laser diode and photodetector to enable laser Doppler-based measurement of blood flow rate, [f] algorithm to continuously analyze measured heart rate values and measured blood flow rate values to determine whether both are below predetermined levels indicative that a cardiac arrest has occurred or is imminent, [g] actuatable audible alarm as well as a vibration (i.e., haptic) alert in the event that a cardiac arrest has occurred or is imminent, [h] sensor to confirm the wearable cardiac arrest detection and alerting device is in contact with subjects skin and accessible to detectable heart beat (e.g., transcutaneous electrical sensor measuring electrical impedance of skin), and [i] wireless communication hardware and software (e.g., Bluetooth ultra-high frequency transmitter) to transmit heart-rate values to accessory cellular phone and programmable device 39.

Still referring to FIG. 9, accessory cellular phone and programmable device 39 includes [a] wireless communication hardware and software (e.g., Bluetooth ultra-high frequency transmitter) to receive heart-rate values from the wearable cardiac arrest detection and alerting device [b] algorithm to continuously analyze measured photon signal data received from the wearable cardiac arrest detection and alerting device to determine whether the measured photon signals are within a predetermined range to confirm that wearable cardiac arrest detection and alerting device is properly functioning and is properly positioned on the individual being monitored and, if measured photon signal levels are within a pre-determined range, continuously derive heart rate value, [c] ultrasound transmitter and receiver to enable Doppler ultrasound-based measurement or laser diode and photodetector to enable laser Doppler-based measurement of blood flow rate, [d] algorithm to continuously analyze measured heart rate values and measured blood flow rate values to determine whether both are below predetermined levels indicative that a cardiac arrest has occurred or is imminent, [e] actuatable audible alarm as well as a vibration (i.e., haptic) alert in the event that a cardiac arrest has occurred or is imminent, [f] global positioning satellite (GPS) based receiver or equivalent position locating component to determine latitude and longitude coordinates of accessory cellular phone and programmable device 39, [g] cellular phone communication component typical of widely used cell phones to issue alert to server along with name of individual, other identification (e.g., unique phone number of accessory cellular phone and programmable device 39), and latitude and longitude coordinates of accessory cellular phone and programmable device 39. The communication of an alert in the event of a cardiac arrest to one or more telephone(s) 46 and/or cellular phone(s) 48 at one or more locations represented by block 44 of first responders is issued first from accessory cellular phone and programmable device 39 to cellular receiving/transmitting tower 198 via wireless communication path 202, then from cellular receiving/transmitting tower 198 to server 206 represented at block 204 via wireless path 210 and finally to one or more telephone(s) 46, and/or one or more cellular phones 48 via wireless communication path 208.

Still referring to FIG. 9, server 206 located at some other physical location represented by block 204 includes [a] wired or wireless communication hardware and software to receive subject's GPS location from accessory cellular phone and programmable device 39 via wireless communication paths 202 and 210, [b] look-up table in software to determine whether wearable cardiac arrest detection and alerting device is at any of the pre-programmed locations frequented by the particular individual being monitored by the wearable cardiac arrest detection and alerting device (e.g., locations such as individual's home, another home, office, fitness facility), [c] access to reverse geocoding data base to identify nearest phone numbers of potential first responders based on subject's GPS-derived location in the event the subject is not at one the frequented pre-programmed locations, [d] cellular phone communication component to call identified phone numbers of first responders identified above in [b] or [c] either the pre-programmed phone numbers if the subject is confirmed by reverse-geocoding to be at one of the including 911 (for use in the U.S.), and [e] audible synthesized speech to annunciate in placed phone calls that a cardiac arrest has occurred, identify the individual's name and specify the exact location of the individual in the form of subject's GPS location or equivalent device derived coordinates and, using reverse geocoding data base software, the actual address of the individual.

The range of dimensions for wearable cardiac arrest detection and alerting device 10 and accessory cellular phone and programmable device 39, as seen in FIGS. 2, 5, 6, 8, and 9 are summarized below in units of inches:
W1=0.25 to 1.50
W2=1.5 to 4.0
L1=0.75 to 2.00
L2=1.50 to 3.50
L3=3.0 to 6.0
t1=0.1 to 0.5

Alternatively, by way of example, but without limitation, the wearable apparatus and system of the present disclosure for the detection and alerting of first responders in the event of occurrence of a cardiac arrest or imminent cardiac arrest may be [a] a wearable cardiac arrest detection and alerting device in the form of a ring positioned on a finger of the hand, [b] a finger-tip mounted device, [c] a device mounted on the lower or upper arm, [d] a device mounted on the torso, [e] a device mounted on the forehead using a headband support, [f] a device mounted on an ear or [g] any other location on the body suitable for non-invasive, transcutaneous measurement of heart rate.

In yet another embodiment of the present disclosure for the detection and alerting of first responders in the event of a cardiac arrest or imminent cardiac arrest, incorporating two or more different apparatus and methods for detecting heart function, one of the two or more wearable sensors may be used to continuously monitor heart function based on detectable electrical signals generated within the human body as a result of electrical impulses generated by the polarization and depolarization of cardiac tissue. The detectable electrical signals are the principle of widely used electrocardiography systems and methods. In this alternative embodiment, the detectable electrical signals are used to detect the wearer's heart function in place of or in addition to the photon sources and based on the principle of photoplethysmography, as well as the ultrasound transducer and receiver based on the principle of Doppler ultrasound blood flow rate measurement, as described with regard to FIGS. 1 through 6, 8, and 9 or laser diode and photodetector based on the principle of laser Doppler blood flow rate measurement. Except for the apparatus and method for detecting heart rate, the electrocardiography-based alternative embodiment of the present disclosure includes all the other components as specified in the foregoing disclosure associated with the photoplethysmography-based wearable cardiac arrest detection and alerting version of the present disclosure (in this regard, see Nemati, E. et. al, A Wireless Wearable ECG Sensor for Long-Term Applications. IEEE Communications Magazine 2012; 50 (1): 36-43), the latter reference incorporated herein by reference.

In yet another embodiment of the present disclosure for the detection and alerting of first responders in the event of a cardiac arrest or imminent cardiac arrest, incorporating two or more different apparatus and methods for detecting heart function, transcutaneous ultrasonography may be used as one of the two apparatus and methods to detect a significant decrease or absence of blood flow in one or more blood vessels of the subject wearing the detection and alerting device. The measured significant decrease or absence of blood flow in one or more blood vessels would be indicative of the occurrence of a cardiac arrest wherein the heart is no longer achieving effective blood circulation in the individual wearing the device.

Figure 10:
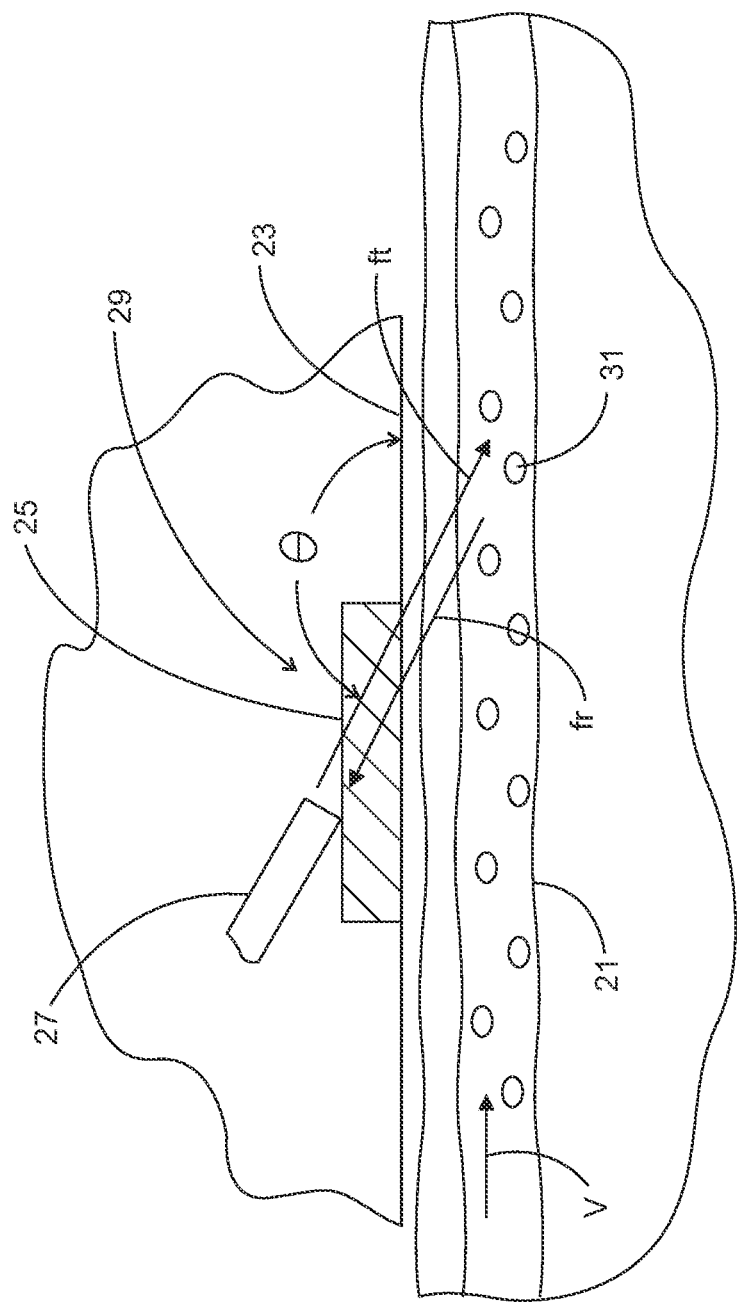
FIG. 10 is a pictorial representation of the Doppler ultrasound based method for the detection of blood flow in tissue.

By way of example but without limitation, Doppler ultrasonography can be used to measure the velocity of blood flow within one or more blood vessels irradiated with ultrasound energy transmitted in a direction either retrograde to or in the direction of blood flow. The Doppler principle states that the frequency of the reflected ultrasound is altered by a moving target in a way that if a sound source moves toward the observer, the reflect sound frequency increases, conversely if the source moves away from the observer, the reflected sound frequency decreases. In an alternative embodiment of the present disclosure based on Doppler echocardiography, a high frequency ultrasound (2 to 20 MHz) beam is generated by a first transducer (not shown) within ultrasound transmission source and receiver 27 that is directed through ultrasound transmissive window 25 towards the red blood cells 31 flowing in one or more blood vessels 21 within the circulatory system as seen in FIG. 10. Still referring to FIG. 10, a second transducer (not shown) within ultrasound transmission source and receiver 27 and in close proximity or combined with the first transducer measures the frequency of the received ultrasound frequency, fr to determine the Doppler frequency shift, Δf, which is the difference between the frequency of the ultrasound transmitted, ft by a first transducer and the frequency of the ultrasound received, fr by a second transducer. The Doppler equation relates the velocity of the moving red blood cells, v to the measured Doppler frequency shift, Δf as follows:

$$v=(\Delta f \cdot c)/(2ft \cdot \cos[\theta])$$ Equation 1 where v is the velocity of the red blood cells, ft is the frequency of the transmitted ultrasound signal, e is the angle between the direction of ultrasound beam and the direction of the moving target (as seen in FIG. 10), fr is the frequency of the ultrasound signal received, c is the velocity of sound in blood (1.54 meters/second) and the Doppler shift, Δf, is define below in Equation N2 and is expressed in units of Hertz.

$$\Delta f = ft - fr$$ Equation 2

In this embodiment based on ultrasonography, a measured blood flow rate below some threshold level (e.g., 0.01 meter/second) would be indicative of the occurrence of a cardiac arrest since the measured blood flow rate would represent that the heart is no longer achieving an adequate level of circulation of blood within in the subject wearing the cardiac arrest detection device. Except for the apparatus and method for detecting heart rate, the Doppler ultrasound-based alternative embodiment of the present disclosure includes all the other components as specified in the foregoing disclosure associated with the photoplethysmography-based wearable cardiac arrest detection and alerting version of the present disclosure (in this regard, see Kuwabara, K., et. al., Wearable Blood Flowmeter Accessory with Low-Power Doppler Signal Processing for Daily-Life Healthcare Monitoring. Conf. Proc. IEEE Eng. Med. Biol. Soc. 2014; 2014: pp. 6274-6277), the latter reference incorporated herein by reference.

An alternative approach to assessing heart function is the measurement of blood flow rate using the laser Doppler method. During blood flow rate measurement using the laser Doppler method, a laser beam emitted from a laser diode is irradiated onto the skin after focusing through a lens. By way of example, the wavelength of the photons emitted by the laser diode may be selected within the range from 700 nm to 1300 nm to achieve adequate penetration into the skin while limiting absorption of irradiated photons by water molecules in the tissue. The irradiated light penetrates the skin to a certain depth and is scattered from the skin, blood vessels, and red blood cells. The frequency of light scattered from the red blood cells is altered by the Doppler effect due to their movement within blood vessels, while light scattered from static or stationary tissue such as skin and connective tissue remains unchanged. The Doppler-shifted and non-shifted light signals interfere on a photodetector and variations in light intensity caused by this interference are detected by the photodetector at a predetermined sampling rate (e.g., 40 kHz sampling rate). The blood flow rate as a proportion of the average velocity and concentration of red blood cells in the capillary from the optical signal. The optical signal detected at the photodetector is transformed with a fast Fourier transformation algorithm that converts measured time-based signal levels to frequency-based signal levels. The first-order moment is calculated by integrating the frequency-weighted optical signal spectrum over the range of 20 Hz to 20 kHz. The first-order moment is divided by the square of mean light intensity measured at the photodetector to obtain an estimate of the average velocity of flowing red blood cells. In this regard, see Iwasaki, W., et. al., Detection of Site-Specific Blood Flow Variation in Humans during Running by a Wearable laser Doppler Flowmeter. Sensors 2015; 15:25507-25519.

Unlike the Doppler Ultrasound apparatus and method, no special coupling agent is required for the laser Doppler apparatus and method between the optical source, photo detector and the subject's skin surface. Also, recent micro-miniaturization development efforts in Japan reported in 2007 confirmed that the size of the laser optical source and detector was reduced to the size that would enable its incorporation within a wristwatch. The measured blood flow rate signal level at the wrist in response to the an occlusion of the upper arm above the wristwatch (using an inflated blood pressure cuff) confirmed a rapid nine-fold decrease in the measured flow rate from 45 to 5 (arbitrary units of flow rate) within 3 seconds. In this regard, see Iwasaki, W., et. al., Miniaturization of a laser Doppler Blood Flow Sensor by System-in-Package Technology: Fusion of an Optical Microelectromechanical Systems Chip and Integrated Circuits. IEEJ Transactions on Electrical and Electronic Engineering 2010, 5: 137-142.

Although the laser Doppler method offers a fast response to sudden absence of blood flow (e.g., within wrist as simulated by the application of sufficient cuff pressure in the upper arm), this method requires power levels that may prevent continuous monitoring for periods, especially for the case wristwatch based device battery components. For that reason, a preferred embodiment for the method for detecting the occurrence of a cardiac arrest only initiates the measurement of the wearer's blood flow rate [a] for a brief measurement duration (e.g., 5 seconds) during periods of detected motionlessness of the wearable device and [b] for a brief measurement duration (e.g., 5 seconds) at regular intervals (e.g., every 10 to 20 minutes) to obtain blood flow rate values to be used for comparison with. blood flow rate values obtained during periods in which the wearable device is motionless.

In yet another embodiment of the present disclosure for the detection and alerting of first responders in the event of a cardiac arrest or imminent cardiac arrest, incorporating two or more different apparatus and methods for detecting heart function, auscultation may be used as one of the two apparatus and methods to measure acoustic signals generated by the heart and/or the lungs indicative of the functionality of the heart. By way of example, a device may be worn around the chest with an acoustic detection transducer (e.g., microphone) positioned against the skin of the subject in the vicinity of the heart and/or lungs to detect acoustic signals generated by a beating heart and/or air entering and existing the lungs. A decrease in the level acoustic signals characteristic of blood flow within a beating heart and/or air flow within lungs that is below a predetermined level would be indicative of the occurrence of a cardiac arrest wherein the heart is no longer inducing audible blood flow in a vital pulsatile manner and/or the lungs are no longer expanding and contracting inducing air flow associated with vital breathing in the individual wearing the device.

In yet another embodiment of the present disclosure, one or more pressure transducers may be positioned on a wearable device to detect the presence of a transient pressure change associated with the pulsatile change in blood pressure induced by a functioning heart, commonly referred to a subject's pulse. By way of example but without limitation, one or more pressure transducers are incorporated into the wristband of a wristwatch style device and transcutaneously positioned in close proximity to an arterial blood vessel within the wrist, such as the radial artery. The one or more pressure transducers provide one or more electronic signals indicative of the presence of the vital change in blood pressure induced by the pulsatile change in blood pressure induced by a functioning heart. An electronic signal level change associated with the pulsatile change in blood pressure induced by a functioning heart that is below a pre-established level of signal level change would be indicative of the occurrence of a cardiac arrest wherein the heart is no longer functioning in a pulsatile manner to generate a pulsatile change in blood pressure and achieve vital blood circulation in the individual wearing the device. In this regard, see Wriskwatch product sold by Emergency Medical Technologies, North Miami Beach, Fla.

Figure 7A:
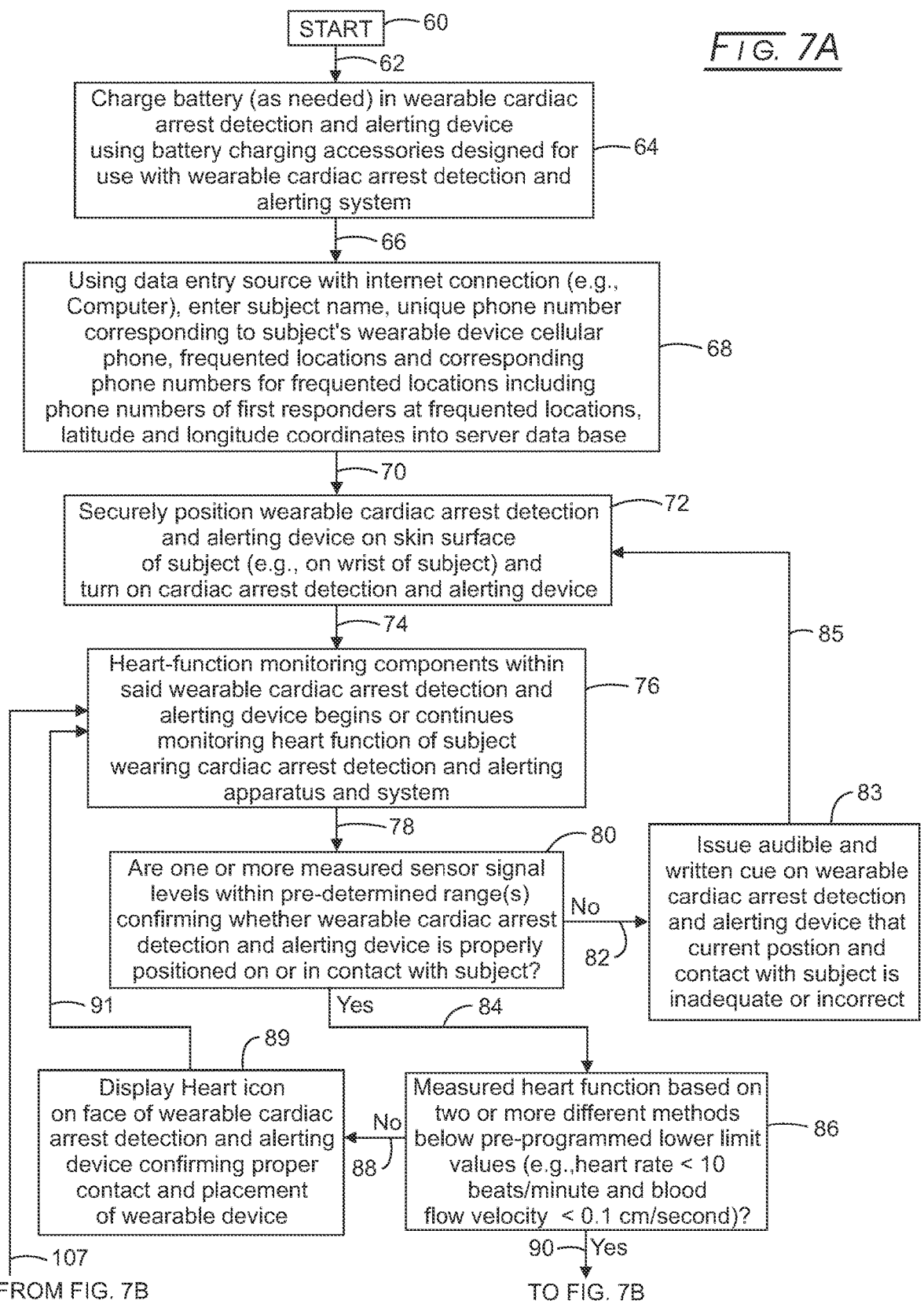
FIGS. 7A and 7B combine as labeled thereon to provide a flow chart describing the operation and use of the wearable cardiac arrest detection and alerting device of a preferred embodiment of the present disclosure as seen in FIGS. 1-4 and 8.
Figure 7B:
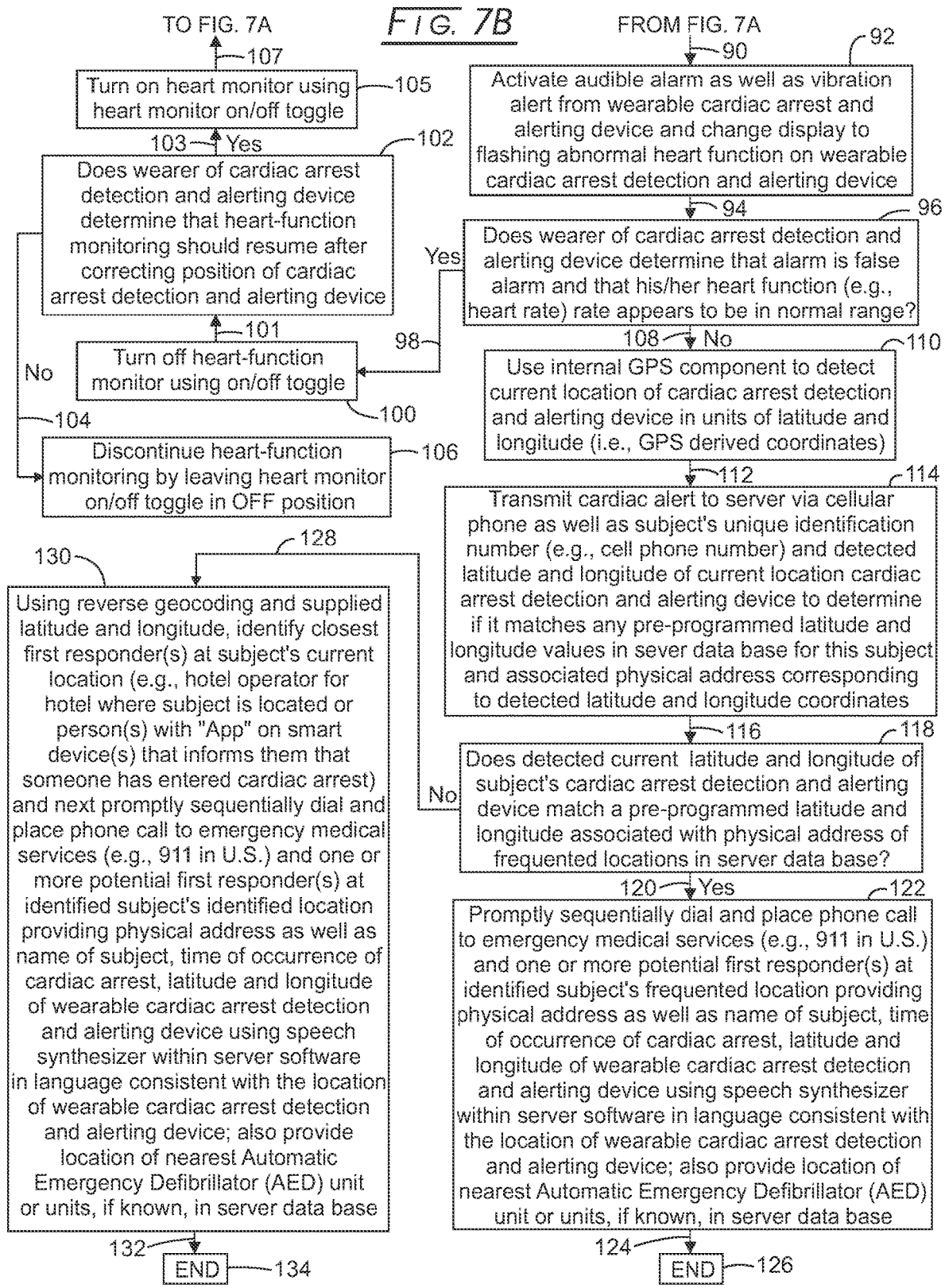

The operation and method of use of the wearable apparatus and system of one of the embodiments of the present disclosure for the detection and alerting of first responders in the event of occurrence of a cardiac arrest or imminent cardiac arrest are set forth in the flow chart represented in FIGS. 7A and 7B in connection with FIGS. 1 through 4 and 8. Those figures should be considered as labeled thereon. Looking to FIG. 7A, the operation of wearable cardiac arrest detection and alerting device 10 commences with the charging of internal battery in wearable cardiac arrest detection and alerting device 10 as seen at arrow 62 and block 64. Once the required batteries are charged, data is entered into wearable cardiac arrest detection and alerting device 10 including the unique phone number of wearable cardiac arrest detection, and alerting device 10, identification (e.g., name) of wearer, addresses of frequently used locations and associated phone numbers into wearable cardiac arrest detection and alerting device 10, as seen at arrow 66 and block 68.

Next, wearable cardiac arrest detection and alerting device is securely positioned on skin surface of an individual and turned on to activate the cardiac arrest detection and alerting device, as seen at arrow 70 and block 72. Heart-function monitoring components within the wearable cardiac arrest detection and alerting device 10 begin continuous monitoring of heart function of individual wearing cardiac arrest detection and alerting device, as seen at arrow 74 and block 76. By way of example, software within wearable cardiac arrest detection and alerting device 10 compares measured one or more sensor signals (e.g., optical signal level) with pre-determined range of one or more sensor signal levels (e.g., optical signal level) to determine whether wearable cardiac arrest detection and alerting device is properly positioned on individual, as seen at arrow 78 and block 80. If measured one or more sensor signals are not within range of pre-determined one or more sensor signal levels, then wearable cardiac arrest detection and alerting device issues audible and display cues as well as a vibration (i.e., haptic) alert to individual being monitored indicating that wearable cardiac arrest detection and alerting device 10 is not properly positioned on individual, as seen at arrow 82 and block 83. As a consequence, the individual is alerted to securely position wearable cardiac arrest detection and alerting device 10, as seen at arrow 85 and block 72 and repeat subsequent steps leading to block 80.

Still referring to FIG. 7A and by way of example, if measured one or more sensor signal levels (e.g., optical signal level) are within range of pre-determined one or more sensor signal levels (e.g., optical signal level), then internal logic in wearable cardiac arrest detection and alerting device is used to determine whether heart function based on measurements using two or more different apparatus and methods (e.g., photoplethysmography based heart rate level and Doppler ultrasound based blood flow rate level or photoplethysmography based heart rate level and laser Doppler based blood flow rate level) are within normal pre-programmed physiological range to provide data necessary to determine whether cardiac arrest or imminent cardiac arrest has occurred, as seen at arrow 84 and block 86. By way of example, if measured heart rate is greater than a pre-programmed physiological lower limit value (e.g., greater than or equal to 10 beats/minute) and measured blood flow rate is greater than a pre-programmed physiological lower limit value (e.g., above 1 cm/second), indicative that no cardiac arrest or imminent cardiac arrest has occurred, then wearable cardiac arrest detection and alerting device continues with monitoring of heart function and display heart icon 20 and (see FIG. 1), as seen at arrow 88 and block 89, and proceeds with continuous monitoring of heart function, as seen at arrow 91 and block 76.

Referring now to FIG. 7B and by way of example, if measured heart rate is less than a pre-programmed physiological lower limit value (e.g., less than 10 beats/minute), indicative that cardiac arrest has occurred or is imminent, then cardiac arrest or imminent cardiac arrest is determined to have occurred. As a result, the internal logic in wearable cardiac arrest detection and alerting device 10 [a] actuates audible alarm as well as a vibration (i.e., haptic) alert and [b] changes display on the face of wearable cardiac arrest detection and alerting device 10 to flashing alert (e.g., "Cardiac Arrest"), as seen at arrow 90 and block 92. During a brief period of pre-programmed duration (e.g., say, 15 seconds) immediately following the start of the audible alarm as well as a vibration (i.e., haptic) alert (referred to hereinafter as the "Alert Check Period"), the individual whose heart function is being monitored has the opportunity to intervene, if the individual determines that their heart function seems to be within a normal range and that a false alarm has occurred, as seen at arrow 94 and block 96. If the individual whose heart function is being monitored determines that their heart function seems to be within a normal range and that the alarm is a false alarm (e.g., due to unintended improper positioning of or contact with wearable cardiac arrest detection and alerting device), then the individual has the opportunity during the Alert Check Period to turn off wearable cardiac arrest detection and alerting device using heart monitor on/off toggle switch and next decides whether wearable cardiac arrest detection and alerting functions of wearable cardiac arrest detection and alerting device 10 should continue. If a false alarm is confirmed by individual, then wearable cardiac arrest detection and alerting device 10 is temporarily turned off as seen at arrow 98 and block 100.

If the individual whose heart function is being monitored decides that wearable cardiac arrest detection and alerting device appears to be malfunctioning, then the individual turns off the wearable cardiac arrest detection and alerting device using heart monitor on/off toggle switch and discontinues its use, as seen at arrow 104 and block 106. Alternatively, if the individual whose heart function is being monitored, decides that wearable cardiac arrest detection and alerting device appears to be functioning normally (e.g., after proper and secure repositioning of the wearable cardiac arrest detection and alerting device on body of individual wearing device), then the individual turns on the wearable cardiac arrest detection and alerting device using heart monitor on/off toggle switch, as seen at arrow 103 and block 105, and heart function monitoring continues, as seen at arrow 107 and block 76 and as seen in FIGS. 7A and 7B.

Still referring to FIG. 7B, if the individual whose heart function is being monitored decides that audible alarm, as well as a vibration (i.e., haptic) alert, issued by wearable cardiac arrest detection and alerting device 10 appears to be a valid alarm or is unconscious or otherwise physically unable to turn off the wearable cardiac arrest detection and alerting device using heart monitor on/off toggle switch, then the audible alarm and procedure for alerting of first responders proceeds. At this time, with the audible alarm continuing, the internal GPS component within wearable cardiac arrest detection and alerting device 10 detects the location of wearable cardiac arrest detection and alerting device 10 in units of latitude and longitude coordinates, as seen at arrow 108 and block 110. Referring to FIGS. 8 and 7B, the detected latitude and longitude coordinate values of wearable cardiac arrest detection and alerting device 10 are transmitted by wearable cardiac arrest detection and alerting device 10 to server 206 using cellular phone communication. Server 206 compares transmitted latitude and longitude coordinate values of wearable cardiac arrest detection and alerting device 10 transmitted with pre-programmed latitude and longitude coordinate values in the database of server 206 to determine whether wearable cardiac arrest detection and alerting device 10 is at a pre-programmed physical address (e.g., home, office, fitness facility), as seen at arrow 112 and block 114. Software within server 206 determines whether wearable cardiac arrest detection and alerting device 10 is at a pre-programmed physical address, as seen at arrow 116 and block 118. If the detected latitude and longitude coordinate values of wearable cardiac arrest detection and alerting device 10 correspond to one of the pre-programmed pair of latitude and longitude coordinate values corresponding to physical address, then server 206 promptly issues phone calls to emergency phone number (e.g., 911 in the U.S.) and all other first responders associated with determined physical address and uses synthesized speech to identify name of individual, time of occurrence of cardiac arrest, physical address, as well as latitude and longitude coordinates, of wearable cardiac arrest detection and alerting device 10, as seen at arrow 120 and block 122.

Alternatively, as seen in FIG. 7B, if the detected pair of latitude and longitude coordinate values of wearable cardiac arrest detection and alerting device 10 do not correspond to one of the pre-programmed pair of latitude and longitude coordinate values corresponding to a physical address, then server 206 utilizes reverse geocoding in combination with latitude and longitude coordinate values transmitted by wearable cardiac arrest detection and alerting device 10 to promptly place telephone calls to emergency phone number (e.g., 911 in the U.S.), as well as one or more potential first responders, identified using reverse geocoding that are determined to be in close proximity to wearable cardiac arrest detection and alerting device 10 based on their respective latitude and longitude coordinate values (e.g., operator at hotel where individual is residing). Server 206 uses synthesized speech to identify name of individual, time of occurrence of cardiac arrest, and the physical address, as well as latitude and longitude coordinates, of wearable cardiac arrest detection and alerting device 10, as seen at arrow 128 and block 130.

In addition to issuing voice synthesized phone calls, text-based messages also can be issued by server 206 to emergency services (e.g., 911) and other first responders on the pre-programmed list wherein the other first responders contacted may be based on detected latitude and longitude coordinates of wearable cardiac arrest detection and alerting device 10. Also, the operation and method of use of the wearable apparatus and system of the present disclosure for the detection and alerting of first responders in the event of occurrence of a cardiac arrest or imminent cardiac arrest, as set forth in the flow chart represented in FIGS. 7A and 7B, also applies to the first, second, and fourth embodiment of the present disclosure for the detection and alerting of first responders in the event of a cardiac arrest, as illustrated pictorially in FIGS. 5, 6, and 9. As seen in FIG. 6, the apparatus and system of a second embodiment of the present disclosure includes a combination of both [a] wearable cardiac arrest detection and alerting device 10 and [b] accessory cellular phone and programmable device 39 maintained within the proximity of the wearable cardiac arrest detection and alerting device (e.g., cellular phone and programmable device 39 within 10 to 100 meters of wearable cardiac arrest detection and alerting device 10) during the period of monitoring. Hence, in the second embodiment of the present disclosure, some of the functions attributed solely to wearable cardiac arrest detection and alerting device 10, as presented in the foregoing description with regard to FIGS. 7A and 7B, are accomplished within the accessory cellular phone and programmable device 39, as seen in FIG. 6 and described in the description presented herein above.

Furthermore, the operation and method of use of the wearable apparatus and system of the present disclosure for the detection and alerting of first responders in the event of occurrence of a cardiac arrest or imminent cardiac arrest, as set forth in the flow chart represented in FIGS. 7A and 7B, also applies to other types of wearable cardiac arrest detection and alerting devices including [a] a wearable cardiac arrest detection and alerting device in the form of a ring positioned on a finger of the hand, [b] a finger-tip mounted device, [c] a device mounted on the lower or upper arm, [d] a device mounted on the torso, [e] a device mounted on the forehead using a headband support, [f] a device mounted on an ear, or [g] any other location on the body suitable for non-invasive, transcutaneous measurement of heart function.

Figure 11A:
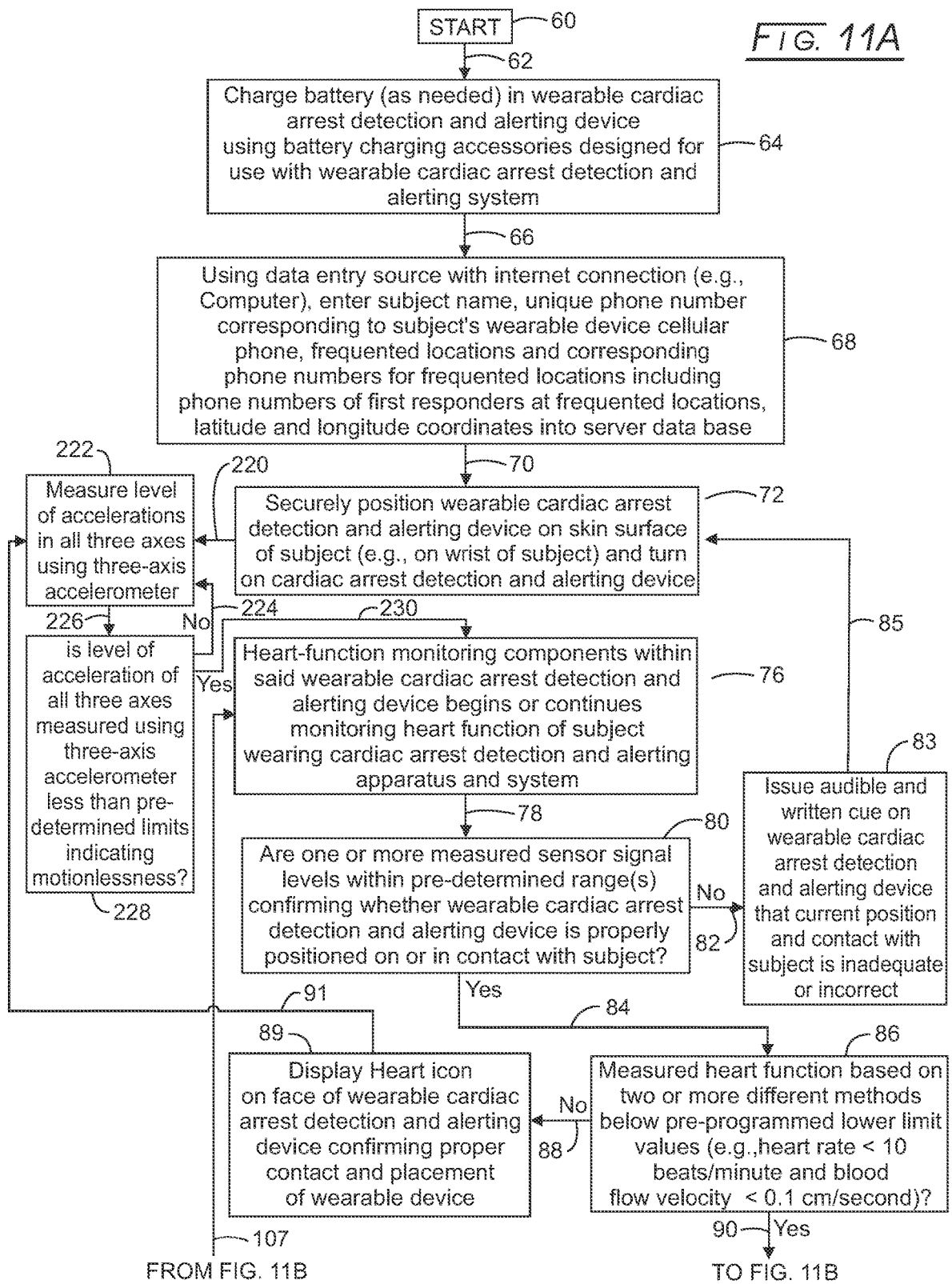

The operation and method of use of the wearable apparatus and system of another embodiment of the present disclosure for the detection and alerting of first responders in the event of occurrence of a cardiac arrest or imminent cardiac arrest are set forth in the flow chart represented in FIGS. 11A and 11B in connection with FIGS. 1 through 4 and 8. Those figures should be considered as labeled thereon. Looking to FIG. 11A, the operation of wearable cardiac arrest detection and alerting device 10 commences with the charging of internal battery in wearable cardiac arrest detection and alerting device 10 as seen at arrow 62 and block 64. Once the required batteries are charged, data is entered into wearable cardiac arrest detection and alerting device 10 including the unique phone number of wearable cardiac arrest detection, and alerting device 10, identification (e.g., name) of wearer, addresses of frequently used locations and associated phone numbers into wearable cardiac arrest detection and alerting device 10, as seen at arrow 66 and block 68.

Next, wearable cardiac arrest detection and alerting device is securely positioned on skin surface of an individual and turned on to activate the cardiac arrest detection and alerting device, as seen at arrow 70 and block 72. Still referring to FIGS. 1, 4, 8, 11A, and 11B, three-axis accelerometer components within the wearable cardiac arrest detection and alerting device 10 begin continuous monitoring of the level of motion of wearable device as seen at arrow 220 and block 222. If the three-axis accelerometer measurements indicate that the level of motion (i.e., acceleration levels) of one or more axes is equal to or greater than a predetermined level indicating that the wearable device is not motionless, as seen at arrow 226 and block 228, then the three-axis accelerometer measurements continue as seen at arrow 224 and block 222.

However, if the three-axis accelerometer measurements indicate that the level of motion in all three axes is less than predetermined levels indicative that the wearable device is in a state of motionlessness, as seen at arrow 226 and block 228, then the heart-function monitoring components incorporated in the wearable device commence measurement of heart function using two or more different methods as seen at arrow 230 and block 76.

By way of example of heart-function monitoring, software within wearable cardiac arrest detection and alerting device 10 compares measured one or more sensor signals (e.g., optical signal level) with pre-determined range of one or more sensor signal levels (e.g., optical signal level) to determine whether wearable cardiac arrest detection and alerting device is properly positioned on individual, as seen at arrow 78 and block 80. If measured one or more sensor signals are not within range of pre-determined one or more sensor signal levels, then wearable cardiac arrest detection and alerting device issues audible and display cues as well as a vibration (i.e., haptic) alert to individual being monitored indicating that wearable cardiac arrest detection and alerting device 10 is not properly positioned on individual, as seen at arrow 82 and block 83. As a consequence, the individual is alerted to securely position wearable cardiac arrest detection and alerting device 10, as seen at arrow 85 and block 72 and repeat subsequent steps leading to block 80.

Still referring to FIG. 11A and by way of example, if measured one or more sensor signal levels (e.g., optical signal level) are within range of pre-determined one or more sensor signal levels (e.g., optical signal level), then internal logic in wearable cardiac arrest detection and alerting device is used to determine whether heart function based on measurements using two or more different apparatus and methods (e.g., photoplethysmography based heart rate level and Doppler ultrasound based blood flow rate level or photoplethysmography based heart rate level and laser Doppler based blood flow rate level) are within normal pre-programmed physiological range to provide data necessary to determine if cardiac arrest or imminent cardiac arrest has occurred, as seen at arrow 84 and block 86. By way of example, if measured heart rate is greater than a pre-programmed physiological lower limit value (e.g., greater than or equal to 10 beats/minute) and measured blood flow rate is greater than a pre-programmed physiological lower limit value (e.g., above 1 cm/second), indicative that no cardiac arrest or imminent cardiac arrest has occurred, then wearable cardiac arrest detection and alerting device continues with monitoring of heart function and display heart icon 20 (see FIG. 1), as seen at arrow 88 and block 89, and proceeds with continuous monitoring of acceleration levels of all three axes using three-axis accelerometer as seen at arrow 91 and block 222.

Referring now to FIG. 11B and by way of example, if measured heart rate is less than a pre-programmed physiological lower limit value (e.g., less than 10 beats/minute), indicative that cardiac arrest has occurred or is imminent, then cardiac arrest or imminent cardiac arrest is determined to have occurred. As a result, the internal logic in wearable cardiac arrest detection and alerting device 10 [a] actuates audible alarm as well as a vibration (i.e., haptic) alert and [b] changes display on the face of wearable cardiac arrest detection and alerting device 10 to flashing alert (e.g., "Cardiac Arrest"), as seen at arrow 90 and block 92. During a brief period of pre-programmed duration (e.g., say, 15 seconds) immediately following the start of the audible alarm as well as a vibration (i.e., haptic) alert (referred to hereinafter as the "Alert Check Period"), the individual whose heart function is being monitored has the opportunity to intervene, if the individual determines that their heart function seems to be within a normal range and that a false alarm has occurred, as seen at arrow 94 and block 96. If the individual whose heart function is being monitored determines that their heart function seems to be within a normal range and that the alarm is a false alarm (e.g., due to unintended improper positioning of or contact with wearable cardiac arrest detection and alerting device), then the individual has the opportunity during the Alert Check Period to turn off wearable cardiac arrest detection and alerting device using heart monitor on/off toggle switch and next decides whether wearable cardiac arrest detection and alerting functions of wearable cardiac arrest detection and alerting device 10 should continue. If individual confirms a false alarm, then wearable cardiac arrest detection and alerting device 10 is temporarily turned off as seen at arrow 98 and block 100.

If the individual whose heart function is being monitored decides that wearable cardiac arrest detection and alerting device appears to be malfunctioning, then the individual turns off the wearable cardiac arrest detection and alerting device using heart monitor on/off toggle switch and discontinues its use, as seen at arrow 104 and block 106. Alternatively, if the individual whose heart function is being monitored, decides that wearable cardiac arrest detection and alerting device appears to be functioning normally (e.g., after proper and secure repositioning of the wearable cardiac arrest detection and alerting device on body of individual wearing device), then the individual turns on the wearable cardiac arrest detection and alerting device using heart monitor on/off toggle switch, as seen at arrow 103 and block 105, and heart function monitoring continues, as seen at arrow 107 and block 76 and as seen in FIGS. 11A and 11B.

Still referring to FIG. 11B, if the individual whose heart function is being monitored decides that audible alarm, as well as a vibration (i.e., haptic) alert, issued by wearable cardiac arrest detection and alerting device 10 appears to be a valid alarm or is unconscious or otherwise physically unable to turn off the wearable cardiac arrest detection and alerting device using heart monitor on/off toggle switch, then the audible alarm and procedure for alerting of first responders proceeds. At this time, with the audible alarm continuing, the internal GPS component within wearable cardiac arrest detection and alerting device 10 detects the location of wearable cardiac arrest detection and alerting device 10 in units of latitude and longitude coordinates, as seen at arrow 108 and block 110. Referring to FIGS. 8 and 11B, the detected latitude and longitude coordinate values of wearable cardiac arrest detection and alerting device 10 are transmitted by wearable cardiac arrest detection and alerting device 10 to server 206 using cellular phone communication. Server 206 compares transmitted latitude and longitude coordinate values of wearable cardiac arrest detection and alerting device 10 transmitted with pre-programmed latitude and longitude coordinate values in the database of server 206 to determine whether wearable cardiac arrest detection and alerting device 10 is at a pre-programmed physical address (e.g., home, office, fitness facility), as seen at arrow 112 and block 114. Software within server 206 determines whether wearable cardiac arrest detection and alerting device 10 is at a pre-programmed physical address, as seen at arrow 116 and block 118. If the detected latitude and longitude coordinate values of wearable cardiac arrest detection and alerting device 10 correspond to one of the pre-programmed pair of latitude and longitude coordinate values corresponding to physical address, then server 206 promptly issues phone calls to emergency phone number (e.g., 911 in the U.S.) and all other first responders associated with determined physical address and uses synthesized speech to identify name of individual, time of occurrence of cardiac arrest, physical address, as well as latitude and longitude coordinates, of wearable cardiac arrest detection and alerting device 10, as seen at arrow 120 and block 122.

Alternatively, as seen in FIG. 11B, if the detected pair of latitude and longitude coordinate values of wearable cardiac arrest detection and alerting device 10 do not correspond to one of the pre-programmed pair of latitude and longitude coordinate values corresponding to a physical address, then server 206 utilizes reverse geocoding in combination with latitude and longitude coordinate values transmitted by wearable cardiac arrest detection and alerting device 10 to promptly place telephone calls to emergency phone number (e.g., 911 in the U.S.), as well as one or more potential first responders, identified using reverse geocoding that are determined to be in close proximity to wearable cardiac arrest detection and alerting device 10 based on their respective latitude and longitude coordinate values (e.g., operator at hotel where individual is residing). Server 206 uses synthesized speech to identify name of individual, time of occurrence of cardiac arrest, and the physical address, as well as latitude and longitude coordinates, of wearable cardiac arrest detection and alerting device 10, as seen at arrow 128 and block 130.

In addition to issuing voice synthesized phone calls, text-based messages also can be issued by server 206 to emergency services (e.g., 911) and other first responders on the pre-programmed list wherein the other first responders contacted may be based on detected latitude and longitude coordinates of wearable cardiac arrest detection and alerting device 10. Also, the operation and method of use of the wearable apparatus and system of the present disclosure for the detection and alerting of first responders in the event of occurrence of a cardiac arrest or imminent cardiac arrest, as set forth in the flow chart represented in FIGS. 11A and 11B, also applies to the first, second, and fourth embodiment of the present disclosure for the detection and alerting of first responders in the event of a cardiac arrest, as illustrated pictorially in FIGS. 5, 6, and 9. As seen in FIG. 6, the apparatus and system of a second embodiment of the present disclosure includes a combination of both [a] wearable cardiac arrest detection and alerting device 10 and [b] accessory cellular phone and programmable device 39 maintained within the proximity of the wearable cardiac arrest detection and alerting device (e.g., cellular phone and programmable device 39 within 10 to 100 meters of wearable cardiac arrest detection and alerting device 10) during the period of monitoring. Hence, in the second embodiment of the present disclosure, some of the functions attributed solely to wearable cardiac arrest detection and alerting device 10, as presented in the foregoing description with regard to FIGS. 11A and 11B, are accomplished within the accessory cellular phone and programmable device 39, as seen in FIG. 6 and described in the description presented herein above.

Furthermore, the operation and method of use of the wearable apparatus and system of the present disclosure for the detection and alerting of first responders in the event of occurrence of a cardiac arrest or imminent cardiac arrest, as set forth in the flow chart represented in FIGS. 11A and 11B, also applies to other types of wearable cardiac arrest detection and alerting devices including [a] a wearable cardiac arrest detection and alerting device in the form of a ring positioned on a finger of the hand, [b] a finger-tip mounted device, [c] a device mounted on the lower or upper arm, [d] a device mounted on the torso, [e] a device mounted on the forehead using a headband support, [f] a device mounted on an ear, or [g] any other location on the body suitable for non-invasive, transcutaneous measurement of heart function.

While the device and method have been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

The invention claimed is:

1. An apparatus for the detection and alerting of first responders in the event of a cardiac arrest which is a wearable cardiac arrest detection and alerting device worn by a wearer having an actual address and a name, comprising:

[a] a first source transmitting photons configured to operate at a first wavelength and second source transmitting photons and configured to operate at a second wavelength, each continuously or intermittently transmitting electromagnetic energy transcutaneously into tissue containing one or more blood vessels for photoplethysmographical determination of a heart rate of the wearer;

[b] one or more photon detectors to continuously and transcutaneously measure photon signal levels associated with said transmitted photons at said first wavelength and at said second wavelength, being transmitted from the tissue containing one or more blood vessels for photoplethysmographical determination of heart rate of the wearer;

[c] a three-axis integrated microelectromechanical system (MEMS) accelerometer configured to generate electrical signal levels corresponding to movement of the wearable cardiac arrest detection and alerting device;

[d] signal processing hardware componentry and software using electrical signals generated by the three-axis integrated microelectromechanical system (MEMS) accelerometer to determine if there is no detectable movement of the wearable device for a predetermined period of time indicative of the wearer being in a state of motionlessness;

[e] electrical components and algorithm to continuously analyze measured photon signals to determine whether the measured photon signals are within a predetermined range to confirm that the wearable cardiac arrest detection and alerting device is properly functioning and is properly positioned on the wearer being monitored and, if the measured photon signal levels are within a pre-determined range, continuously derive the heart rate of the wearer;

[f] one or more photon emitting laser diodes and one or more photodetectors to enable laser Doppler-based measurement of blood flow rate by detection of [i] Doppler-shifted frequency of light scattered from red blood cells due to their movement within blood vessels; and [ii] non-shifted frequency of light from the tissue signal interference on a photodetector and variations in light intensity caused by the interference at a predetermined sampling rate;

[g] electrical components and algorithm to transform measured time-based signal levels corresponding to variations in light intensity to frequency-based signal levels whose optical signal spectrum is integrated over a predetermined frequency range to estimate the velocity of flowing red blood cells;

[h] electrical components and algorithm to continuously analyze the measured heart rate and the measured blood flow rate to determine if both the measured heart rate and the blood flow rate level are below predetermined levels indicative of a cardiac arrest;

[i] an actuatable audible alarm in the event of a determined cardiac arrest;

[j] a global positioning satellite (GPS) based receiver to determine latitude and longitude of the wearable cardiac arrest detection and alerting device;

[k] a look-up table in software of locations frequented by the wearer to determine whether wearable cardiac arrest detection and alerting device is at any of the locations frequented by the individual;

[l] a cellular phone communication component to place calls in the event of a determined cardiac arrest to a pre-programmed, pre-established list of phone numbers in a lookup table;

[m] electrical components and algorithm to generate audible synthesized speech used in issued phone calls to annunciate occurrence of a cardiac arrest, identify the wearer's name and specify the exact location of the wearer in the form of his or her GPS device determined coordinates and, if the individual wearer is at a location with pre-established GPS derived coordinates, the actual address of the wearer;

[n] a non transitory storage medium to store lower limit values of heart rate, blood flow rate and identification indicia for the wearable device;

[o] the GPS determined latitude and longitude coordinates of the wearable device;

[p] a rechargeable battery;

[q] battery charging terminals for coupling to an inductive battery charging component;

[r] an alert indicative of a determined cardiac arrest; and

[s] an on/off button on wearable device to enable cancellation of an alarm in the event of a false detection of a cardiac arrest.

2. The apparatus of claim 1, wherein the photons emitted by the one or more photon emitting laser diodes have wavelengths are within the range from 700 to 1300 nanometers.

3. The apparatus of claim 1, wherein said first wavelength is in the range between 600 nanometers and 760 nanometers and said second wavelength length is in the range between 800 nanometers and 950 nanometers.

4. The apparatus of claim 1, wherein said first wavelength is 560 nanometers and said second wavelength length is 577 nanometers.

5. The apparatus of claim 1, wherein the said optical signal spectrum is integrated over the frequency range from 20 Hz to 20 kHz.

6. An apparatus for the detection and alerting of first responders in the event of a cardiac arrest which is a wearable cardiac arrest detection and alerting device worn by a wearer having an actual address and a name, comprising:

[a] a three-axis integrated microelectromechanical system (MEMS) accelerometer configured to generate electrical signal levels corresponding to movement of wearable cardiac arrest detection and alerting device;

[b] signal processing hardware componentry and software using electrical signals generated by three-axis integrated microelectromechanical system (MEMS) accelerometer to determine if there is no detectable movement of the wearable device for a predetermined period referred to the wearer being in a state of motionlessness;

[c] one or more photon emitting laser diodes and one or more photodetectors to enable laser Doppler-based measurement of blood flow rate by detection of [i] Doppler-shifted frequency of light scattered from red blood cells due to their movement within blood vessels and [ii] non-shifted frequency of light from the tissue signal interference on a photodetector and variations in light intensity caused by the interference at a predetermined sampling rate;

[d] electrical components and algorithm to transform the measured time-based signal levels corresponding to variations in light intensity to frequency-based signal levels whose optical signal spectrum is integrated over a predetermined frequency range to estimate the velocity of flowing red blood cells;

[e] electrical components and algorithm to continuously analyze the measured heart rate value and the measured blood flow rate to determine if both the measured heart rate and the blood flow rate level are below predetermined levels indicative of a cardiac arrest;

[f] an actuatable audible alarm in the event of a determined cardiac arrest;

[g] a global positioning satellite (GPS) based receiver to determine latitude and longitude of wearable cardiac arrest detection and alerting device;

[h] a look-up table in software of locations frequented by the wearer to determine whether wearable cardiac arrest detection and alerting device is at any of the locations frequented by the individual;

[i] a cellular phone communication component to place calls in the event of a determined cardiac arrest to a pre-programmed, pre-established list of phone numbers;

[j] electrical components and algorithm to generate audible synthesized speech used in issued phone calls to annunciate occurrence of a cardiac arrest, identify the wearer's name and specify the exact location of the wearer in the form of his or her GPS determined coordinates and, if the wearer is at a location with pre-established GPS determined coordinates, the actual address of the wearer;

[k] a non transitory storage medium to store lower limit values of heart rate, blood flow rate and identification indicia for the wearable device;

[l] the GPS determined latitude and longitude coordinates of the wearable device;

[m] a rechargeable battery;

[n] battery charging terminals for coupling to an inductive battery charging component;

[o] an alert indicative of a determined cardiac arrest, and

[p] an on/off button on wearable device to enable cancellation of an alarm in the event of a false detection of a cardiac arrest.

7. The apparatus of claim 6, wherein the photons emitted by the one or more photon emitting laser diodes have wavelengths within the range from 700 to 1300 nanometers.

8. The apparatus of claim 6, wherein the said optical signal spectrum is integrated over the frequency range from 20 Hz to 20 kHz.

9. A system for the detection and alerting of first responders in the event of a cardiac arrest which is a wearable cardiac arrest detection and alerting device worn by a wearer having an actual address and a name, comprising:

[a] a first source transmitting photons configured to operate at a first wavelength and second source transmitting photons and configured to operate at a second wavelength, each continuously or intermittently transmitting electromagnetic energy transcutaneously into tissue containing one or more blood vessels for photoplysmographical determination of heart rate;

[b] one or more photon detectors to continuously and transcutaneously measure photon signal levels associated with said transmitted photons at said first wavelength and said second wavelength, being transmitted from the tissue containing one or more blood vessels for photoplethysmographical determination of heart rate;

[c] a three-axis integrated microelectromechanical system (MEMS) accelerometer configured to generate electrical signal levels corresponding to movement of wearable cardiac arrest detection and alerting device;

[d] signal processing hardware componentry and software using electrical signals generated by three-axis integrated microelectromechanical system (MEMS) accelerometer to determine if there is no detectable movement of the wearable device for a predetermined period referred to the wearer being in a state of motionlessness;

[e] electrical components and algorithm to continuously analyze the measured photon signals to determine whether the measured photon signals are within a predetermined range to confirm that wearable cardiac arrest detection and alerting device is properly functioning and is properly positioned on the wearer being monitored and, if the measured photon signal levels are within a pre-determined range, continuously derive heart rate;

[f] one or more photon emitting laser diodes and one or more photodetectors to enable laser Doppler-based measurement of blood flow rate by detection of [i] Doppler-shifted frequency of light scattered from red blood cells due to their movement within blood vessels; and [ii] non-shifted frequency of light from the tissue signal interference on a photodetector and variations in light intensity caused by the interference at a predetermined sampling rate;

[g] electrical components and algorithm to transform the measured time-based signal levels corresponding to variations in light intensity to frequency-based signal levels whose optical signal spectrum is integrated over a predetermined frequency range to estimate the velocity of flowing red blood cells;

[h] electrical components and algorithm to continuously analyze the measured heart rate and the measured blood flow rate to determine if both the measured heart rate and the blood flow rate level are below predetermined levels indicative of a cardiac arrest;

[i] an actuatable audible alarm in the event of a cardiac arrest;

[j] a global positioning satellite (GPS) based receiver to determine latitude and longitude of the wearable cardiac arrest detection and alerting device;

[k] a look-up table in software of locations frequented by the wearer to determine whether wearable cardiac arrest detection and alerting device is at any of the locations frequented by the wearer;

[l] a cellular phone communication component to place calls in the event a determined cardiac to a pre-programmed, pre-established list of phone numbers;

[m] electrical components and algorithm to generate audible synthesized speech used in issued phone calls to annunciate occurrence of a cardiac arrest, identify the wearer's name and specify the exact location of the wearer in the form of his or her GPS determined coordinates and, if the wearer is at a location with pre-established GPS derived coordinates, the actual address of the wearer;

[n] a non transitory storage medium to store lower limit values of heart rate, blood flow rate and identification indicia for the wearable device;

[o] the GPS determined latitude and longitude coordinates of the wearable device;

[p] a rechargeable battery;

[q] battery charging terminals for coupling to an inductive battery charging component;

[r] an alert indicative of a cardiac arrest, and

[s] an on/off button on wearable device to enable cancellation of an alarm in the event of a false detection of a cardiac arrest, and

[t] a server comprising a machine and computer software that includes a pre-programmed set of computer instructions that waits for an alert via cellular communication from a wearable device and responds to the alert according to the pre-programmed set of computer instructions.

10. The system of claim 9, wherein the set of computer instructions within server include phone numbers of the nearest first responder(s) based on the subject's GPS-based location as well as the phone number of the identified emergency medical services associated with the country in which the subject is located.

11. The system of claim 9, wherein the photons emitted by the one or more photon emitting laser diodes have wavelengths within the range from 700 to 1300 nanometers.

12. The system of claim 9, wherein said first wavelength is in the range between 600 nanometers and 760 nanometers and said second wavelength length is in the range between 800 nanometers and 950 nanometers.

13. The system of claim 9, wherein said first wavelength is 560 nanometers and said second wavelength length is 577 nanometers.

14. The system of claim 9, wherein the said optical signal spectrum is integrated over the frequency range from 20 Hz to 20 kHz.

15. A system for the detection and alerting of first responders in the event of a cardiac arrest which is a wearable cardiac arrest detection and alerting device worn by a wearer having an actual address and a name, comprising:

[a] a three-axis integrated microelectromechanical system (MEMS) accelerometer configured to generate electrical signal levels corresponding to movement of wearable cardiac arrest detection and alerting device;

[b] signal processing hardware componentry and software using electrical signals generated by three-axis integrated microelectromechanical system (M EMS) accelerometer to determine if there is no detectable movement of the wearable device for a predetermined period referred to the wearer being in a state of motionlessness;

[c] one or more photon emitting laser diodes and one or more photodetectors to enable laser Doppler-based measurement of blood flow rate by detection of [i] Doppler-shifted frequency of light scattered from red blood cells due to their movement within blood vessels and [ii] non-shifted frequency of light from the tissue signal interference on a photodetector and variations in light intensity caused by the interference at a predetermined sampling rate;

[d] electrical components and algorithm to transform the measured time-based signal levels corresponding to variations in light intensity to frequency-based signal levels whose optical signal spectrum is integrated over a predetermined frequency range to estimate the velocity of flowing red blood cells;

[e] electrical components and algorithm to continuously analyze the measured heart rate value and the measured blood flow rate to determine if both the measured heart rate and the blood flow rate level are below predetermined levels indicative of a cardiac arrest has occurred or is imminent;

[f] an actuatable audible alarm in the event of a cardiac arrest;

[g] a global positioning satellite (GPS) based receiver to determine latitude and longitude of wearable cardiac arrest detection and alerting device;

[h] a look-up table in software of locations frequented by the wearer to determine whether wearable cardiac arrest detection and alerting device is at any of the locations frequented by the wearer;

[i] a cellular phone communication component to place calls in the event of a cardiac arrest to a pre-programmed, pre-established list of phone numbers;

[j] electrical components and algorithm to generate audible synthesized speech used in issued phone calls to annunciate occurrence of a cardiac arrest, identify the wearer's name and specify the exact location of the wearer in the form of his or her GPS determined coordinates and, if the wearer is at a location with pre-established GPS determined coordinates, the actual address of the wearer;

[k] a non transitory storage medium to store lower limit values of heart rate, blood flow rate and identification indicia for the wearable device;

[l] the GPS determined latitude and longitude coordinates of the wearable device;

[m] a rechargeable battery;

[n] battery charging terminals for coupling to an inductive battery charging component;

[o] an alert indicative of a cardiac arrest event, and

[p] an on/off button on wearable device to enable cancellation of an alarm in the event of a false detection of a cardiac arrest; and

[q] a server comprising a machine and computer software that waits for an alert via cellular communication from a wearable device and responds to an alert according to a pre-programmed set of computer instructions.

16. The system of claim 15, wherein the set of computer instructions within server include phone numbers of the nearest first responder(s) based on the subject's GPS-based location as well as the phone number of the identified emergency medical services associated with the country in which the subject is located.

17. The system of claim 15, wherein the photons emitted by the one or more photon emitting laser diodes have wavelengths within the range from 700 to 1300 nanometers.

18. The system of claim 15, wherein the said optical signal spectrum is integrated over the frequency range from 20 Hz to 20 kHz.

* * * * *